United States Patent [19]
Tsien et al.

[11] Patent Number: 5,741,657
[45] Date of Patent: Apr. 21, 1998

[54] FLUOROGENIC SUBSTRATES FOR β-LACTAMASE AND METHODS OF USE

[75] Inventors: Roger Y. Tsien, La Jolla; Gregor Zlokarnik, San Diego, both of Calif.

[73] Assignee: The Regents of the University of California, Oakland, Calif.

[21] Appl. No.: 407,544

[22] Filed: Mar. 20, 1995

[51] Int. Cl.$^6$ .......................... C12Q 1/34; C07D 501/00; C07D 501/14
[52] U.S. Cl. .......................... 435/18; 435/805; 540/222; 540/205
[58] Field of Search .................. 435/18, 805; 540/222, 540/205

[56] References Cited

U.S. PATENT DOCUMENTS

| | | | |
|---|---|---|---|
| 4,234,683 | 11/1980 | McMillan | 435/18 |
| 4,383,032 | 5/1983 | Stahl et al. | 435/23 |
| 4,448,880 | 5/1984 | Schindlen et al. | 435/18 |
| 4,740,459 | 4/1988 | Chen et al. | 435/18 |
| 4,760,018 | 7/1988 | Charm | 435/7 |
| 4,764,462 | 8/1988 | Bredehorst et al. | 435/18 |
| 4,978,613 | 12/1990 | Bieniarz et al. | 435/18 |
| 5,162,524 | 11/1992 | Farina et al. | 540/358 |
| 5,264,346 | 11/1993 | Cen | 435/25 |
| 5,338,843 | 8/1994 | Quante et al. | 540/222 |
| 5,514,561 | 5/1996 | Quante et al. | 435/18 |
| 5,583,217 | 12/1996 | Quante et al. | 540/225 |

FOREIGN PATENT DOCUMENTS

| | | |
|---|---|---|
| 0 053 541 A1 | 6/1982 | European Pat. Off. . |
| 0 354 757 A2 | 2/1990 | European Pat. Off. . |

OTHER PUBLICATIONS

A. Yaron et al., Intramolecularly Quenched Fluorogenic Substrates for Hydrolytic Enzymes, Anal. Biochem. 1979, 95, 228–235.

Kuo et al., "Iodometric Method for Detection of β-Lactamase Activity in Yeast Cells Carrying Ampicillin Resistance Gene in Chimeric Plasmids", *Analytical Biochemistry*, 177, pp. 165–167 (1989).

Simonen et al., "The Role of the Carrier Protein and Disulfide Formation in the Folding of β-Lactamase Fusion Proteins in the Endoplasmic Reticulum of Yeast", *Jrnl. Biol. Chem.* 269:13887–13892, (1994).

De Sutter et al., "A Bifunctional Murine::Human Chimeric Antibody With One Antigen–Binding Arm Replaced By Bacterial β–Lactamase", *Mol. Immunol.* vol. 31, No. 4 pp. 261–267 (1994).

Rodrigues, et al. "Development of a Humanized Disulfide–stabilized Anti–p185HER2 Fv–β–Lactamase Fusion Protein for Activation of a Cephalosporin Doxorubicin Prodrug", *Cancer Res.*, 55:63–70 (1995).

L.A. Castelli et al., "High–level secretion of correctly processed β–lactamase from *Saccharomyces cerevisiae* using a high–copy–number secretion vector", *Gene* 142 (1994) pp. 113–117.

M. Wiedmann et al., "Xenopus oocytes can secrete bacterial β–lactamase", *Nature*, vol. 309, Jun. 14, 1984, pp. 637–639.

Charles P. Cartwright et al., "Use of β–Lactamase as a Secreted Reporter of Promoter Function in Yeast", *Yeast*, vol. 10:497–508 (1994).

Kay Simon et al., "Translocation of Globin Fusion Proteins across the Endoplasmic Reticulum Membrane in *Xenopus laevis* Oocytes", *The Journal of Cell Biology*, vol. 104, May 1987, pp. 1165–1172.

Sui–Lam Wong, "Development of an inducible and enhancible expression and secretion system in *Bacillus subtilis*", *Gene*, 83 (1989) pp. 215–223.

Hans R. Waterham et al., "The *Hansenula polymorpha* PER1 Gene Is Essential for Peroxisome Biogenesis and Encodes a Peroxisomal Matrix Protein With Both Carboxy–and Amino–terminal Targeting Signals", *The Journal of Cell Biology*, vol. 127, No. 3, Nov. 1994, pp. 737–749.

Pablo D. Garcia et al., "Wild Type Mutant Signal Peptides of *Escherichia coli* Outer Membrane Lipoprotein Interact with Equal Efficiency with Mammalian Recognition Particle", *The Journal of Biological Chemistry*, vol. 262, No. 20, Issue of Jul. 15, 1987, pp. 9463–9468.

Gorman, C.M. et al., *Mol. Cell Biol.* 2: 1044–1051 (1982).

Alam, J. and Cook, J.L., *Anal.Biochem.* 188: 245–254, (1990).

Rosenthal, N., *Methods Enzymol.* 152: 704–720 (1987).

(List continued on next page.)

Primary Examiner—Gary L. Kunz
Assistant Examiner—Friedrich N. Burnett
Attorney, Agent, or Firm—Fish & Richardson P.C.

[57] ABSTRACT

Fluorogenic substrates of the general formula I

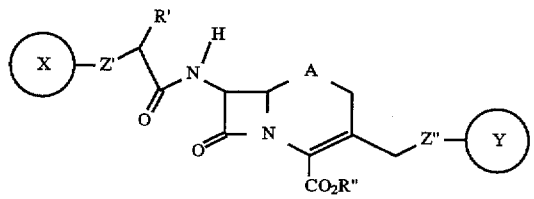

in which one of X and Y is a fluorescent donor moiety and the other is a quencher (which may or may not re-emit); R' is selected from the group consisting of H, lower (i.e., alkyl of 1 to about 5 carbon atoms) and $(CH_2OH)_nOH$, in which n is 0 or an integer from 1 to 5; R" is selected from the group consisting of H, physiologically acceptable metal and ammonium cations, $-CHR^2OCO(CH_2)_nCH_3$, $-CHR^2OCOC(CH_3)_3$, acylthiomethyl, acyloxy-alpha-benzyl, delta-butyrolactonyl, methoxycarbonyloxymethyl, phenyl, methylsulphinylmethyl, beta-morpholinoethyl, dialkylaminoethyl, acyloxyalkyl, dialkylaminocarbonyloxymethyl and aliphatic, in which $R^2$ is selected from the group consisting of H and lower alkyl; A is selected from the group consisting of S, O, SO, $SO_2$ and $CH_2$; and Z' and Z" are linkers for the fluorescent donor and quencher moieties. The substrates are useful in conjunction with β-lactamase as reporter gene in a wide range of assays, for example to determine protein localization or bacterial resistance.

18 Claims, 6 Drawing Sheets

OTHER PUBLICATIONS

Shiau, A. and Smith, J.M., *Gene* 67: 295–299 (1988).

Stryer, L. Introduction to enzymes. In: *Biochemistry*, New York: W. H. Freeman and company, 1981, pp. 103–134.

Chang, Y.H. et al., *Proc.Natl.Acad.Sci.USA* 87: 2823–2827 (1990).

Tsien, R.Y. and Waggoner, A.S. Fluorophores, for confocal microscopy: Photophysics and photochemistry. In: *Handbook of Biological Confocal Microscopy*, edited by Pawley, J.B. Plenum Publishing Corporation, 1990, pp. 169–178.

Bundgaard, H., *Design of prodrugs*, Elsevier Science publishers (1985).

Ferres, H. (1980) *Chem. Ind.* Jun.:435–440.

Christensen, H. et al., *Biochem. J.* 266: 853–861 (1990).

O'Callaghan, C.H. et al., *Antimicrob.Agents.Chemother.* 8: 57–63, (1968).

Stratton, C.W., *J.Antimicrob.Chemother.* 22, Suppl. A: 23–35 (1988).

Richmond, M.H. et al., *Ann.N.Y.Acad.Sci.* 182: 243–257 (1971).

Ambler, R.P., *Phil.Trans.R.Soc.Lond.[Ser.B.]* 289: 321–331 (1980).

Castagnoli, L. et al., *Genet.Res.* 40: 217–231 (1982).

Pratt, R.F. and Govardhan, C.P., *Proc.Natl.Acad.Sci.USA* 81: 1302–1306 (1984).

Murphy, B.P. and Pratt, R.F., *Biochemistry* 30: 3640–3649 (1991).

Bush, K. and Sykes, R.B., *Antimicrob.Agents.Chemother.* 30:6–10 (1986).

Jansen, A.B.A. and Russell, T.J., *J.Chem.Soc.* 2127–2132, (1965).

Jones, R.N. et al., *J.Clin.Microbiol.* 15: 677–683 (1982).

O'Callaghan, C.H. et al., *Antimicrob.Agents.Chemother.* 1:283–288 (1972).

Richmond, M.H. and Sykes, R.B., *Adv.Microb.Physiol.* 9: 31–88 (1973).

Kadonaga, J.T. et al., *J.Biol.Chem.* 259: 2149–2154 (1984).

Sutcliffe, J.G., *Proc.Natl.Acad.Sci.USA* 75: 3737–3741 (1978).

Forster, T. (1948) *Ann.Physik* 2: 55–75.

Lakowicz, J.R., *Principles of Fluorescence Spectroscopy*, New York:Plenum Press (1983) Herman, B., Resonance energy transfer microscopy, in: *Fluorescence Microscopy of Living Cells in Culture, Part B, Methods in Cell Biology*, vol. 30, ed.

Taylor, D.L. & Wang, Y.-L., San Diego: Academic Press (1989), pp. 219–243.

Turro, N.J., *Modern Molecular Photochemistry*, Menlo Part: Benjamin/Cummings Publishing Co., Inc. (1978), pp. 296–361.

dos Remedios, C.G. et al. (1987) *J. Muscle Research and Cell Motility* 8:97–117.

Bojarski, C. and Sienicki, K. Energy transfer and migration in fluorescent solutions. In: *Photochemistry and Photophysics*, edited by Rabek, J.F. Boca Raton: CRC Press, Inc., 1990, pp. 1–57.

Page, M.I., *Adv.Phys.Org.Chem.* 23: 165–270 (1987).

Tsien, R.Y. (1986) New tetracarboxylate chelators for fluorescence measurement and photochemical manipulation of cytosolic free calcium concentrations, in: *Optical Methods in Cell Physiology*, ed. de Weer, P. & Salzberg, B., New York:Wiley, pp. 327–345.

Van Hejningen, E. and Brown, C.N., *J. Med.Chem.* 8: 174–181 (1965).

Japanese Patent Kokai 75/18494, CA 85, 97320d.

Bunnell, C.A., et al. Industrial manufacture of cephalosporins. In: *Beta–Lactam Antibiotics for Clinical Use. Series: Clinical Pharmacology* vol. 4, edited by Queener, S.F., Webber, J.A. and Queener, S.W. New York: M. Dekker, 1986, pp. 255–283.

FLUOROGENIC SUBSTRATES FOR β-LACTAMASE AND METHODS OF USE

This invention was made with Government support under Grant No. NS-27177, awarded by the National Institutes of Health. The Government has certain rights in this invention.

BACKGROUND OF THE INVENTION

The present invention relates generally to the fields of chemistry and biology. More particularly, the present invention relates to compositions and methods for use in measuring gene expression.

A reporter gene assay measures activity of a gene's promoter. It takes advantage of molecular biology techniques, which allow one to put heterologous genes under the control of any promoter and introduce the construct into the genome of a mammalian cell [Gorman, C. M. et al., *Mol. Cell Biol.* 2: 1044–1051 (1982); Alam, J. and Cook, J. L., *Anal. Biochem.* 188: 245–254, (1990)]. Activation of the promoter induces the reporter gene as well as or instead of the endogenous gene. By design the reporter gene codes for a protein that can easily be detected and measured. Commonly it is an enzyme that converts a commercially available substrate into a product. This conversion is conveniently followed by either chromatography or direct optical measurement and allows for the quantification of the amount of enzyme produced.

Reporter genes are commercially available on a variety of plasmids for the study of gene regulation in a large variety of organisms [Alam and Cook, supra]. Promoters of interest can be inserted into multiple cloning sites provided for this purpose in front of the reporter gene on the plasmid [Rosenthal, N., *Methods Enzymol.* 152: 704–720 (1987); Shiau, A. and Smith, J. M., *Gene* 67: 295–299 (1988)]. Standard techniques are used to introduce these genes into a cell type or whole organism [e.g., as described in Sambrook, J., Fritsch, E. F. and Maniatis, T. Expression of cloned genes in cultured mammalian cells. In: *Molecular Cloning*, edited by Nolan, C. New York: Cold Spring Harbor Laboratory Press, 1989]. Resistance markers provided on the plasmid can then be used to select for successfully transfected cells.

Ease of use and the large signal amplification make this technique increasingly popular in the study of gene regulation. Every step in the cascade DNA→RNA→Enzyme→Product→Fluorescence or Color amplifies the next one in the sequence. The further down in the cascade one measures, the more signal one obtains.

In an ideal reporter gene assay, the reporter gene under the control of the promoter of interest is transferred into cells, either transiently or stably. Receptor activation leads to a change in enzyme levels via transcriptional and translational events. The amount of enzyme present can be measured via its enzymatic action on a substrate. The substrate is a small uncharged molecule that, when added to the extracellular solution, can penetrate the plasma membrane to encounter the enzyme. A charged molecule can also be employed, but the charges need to be masked by groups that will be cleaved by endogenous cellular enzymes (e.g., esters cleaved by cytoplasmic esterases).

For a variety of reasons, the use of substrates which exhibit changes in their fluorescence spectra upon interaction with an enzyme are particularly desirable. In some assays, the fluorogenic substrate is converted to a fluorescent product. Alternatively, the fluorescent substrate changes fluorescence properties upon conversion at the reporter enzyme. The product should be very fluorescent to obtain maximal signal, and very polar, to stay trapped inside the cell.

To achieve the highest possible sensitivity in a reporter assay one has to maximize the amount of signal generated by a single reporter enzyme. An optimal enzyme will convert $10^5$ substrate molecules per second under saturating conditions [Stryer, L. Introduction to enzymes. In: *Biochemistry, New York: W. H. Freeman and company*, 1981, pp. 103–134]. β-Lactamases will cleave about $10^3$ molecules of their favorite substrates per second [Chang, Y. H. et al., *Proc. Natl. Acad. Sci. USA* 87: 2823–2827 (1990)]. Using a fluorogenic substrate one can obtain up to $10^6$ photons per fluorescent product produced, depending on the type of dye used, when exciting with light of the appropriate wavelength. The signal terminates with the bleaching of the fluorophore [Tsien, R. Y. and Waggoner, A. S. Fluorophores for confocal microscopy: Photophysics and photochemistry. In: *Handbook of Biological Confocal Microscopy*, edited by Pawley, J. B. Plenum Publishing Corporation, 1990, pp. 169–178]. These numbers illustrate the theoretical magnitude of signal obtainable in this type of measurement. In practice a minute fraction of the photons generated will be detected, but this holds true for fluorescence, bioluminescence or chemiluminescence. A good fluorogenic substrate for a reporter enzyme has to have a high turnover at the enzyme in addition to good optical properties such as high extinction and high fluorescence quantum yield.

It is an object of the present invention to provide substrates and reporter gene product/substrate combinations which obviate some of the problems encountered with prior art assay systems.

SUMMARY OF THE INVENTION

In accordance with the present invention, fluorogenic substrates are provided of the general formula I

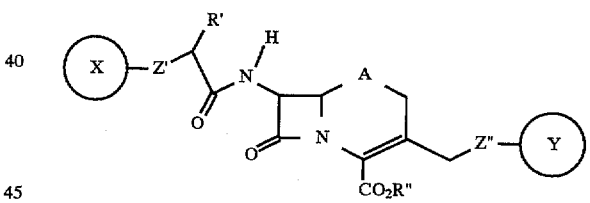

in which one of X and Y is a fluorescent donor moiety and the other is a quencher (which may or may not re-emit); R' is selected from the group consisting of H, lower (i.e., alkyl of 1 to about 5 carbon atoms), $(CH_2)_nOH$ and $(CH_2)_nOOC(CH_2)_mCH_3$, in which each of n and m is independently 0 or an integer from 1 to 5; R" is selected from the group consisting of H, physiologically-acceptable metal and ammonium cations, $-CHR^2OCO(CH_2)_nCH_3$, $-CHR^2OCOC(CH_3)_3$, acylthiomethyl, acyloxy-alpha-benzyl, delta-butyrolactonyl, methoxycarbonyloxymethyl, phenyl, methylsulphinylmethyl, beta-morpholinoethyl, dialkylaminoethyl, acyloxyalkyl, dialkylaminocarbonyloxymethyl and aliphatic groups (e.g., alkyl of 1 to about 10 carbon atoms) [see, e.g., Bundgaard, H., *Design of prodrugs*, Elsevier Science publishers (1985); *Bioreversible Carriers in Drug Design*, New York:Pergamon Press (1987); Ferres, H. (1980) *Chem. Ind.* June:435–440] in which $R^2$ is selected from the group consisting of H and lower alkyl; A is selected from the group consisting of S, O, SO, $SO_2$ and $CH_2$; and Z' and Z" are linkers (as hereinafter defined) for the fluorescent donor and quencher moieties. When R" is H, the fluorogenic substrate may be converted to a pharmaceutically acceptable non-toxic salt in a manner well known per se to those skilled in the art. Fluorescent donor moieties of particular interest include coumarins and fluoresceins; particular quenchers of interest include fluoresceins, rhodols and rhodamines. The substrates are useful in conjunction with β-lactamase as reporter gene in a wide range of assays, for example to determine protein localization or bacterial resistance.

BRIEF DESCRIPTION OF THE DRAWINGS

The invention may be better understood with reference to the accompanying drawings, in which.

DETAILED DESCRIPTION OF THE INVENTION

Figure 1A:
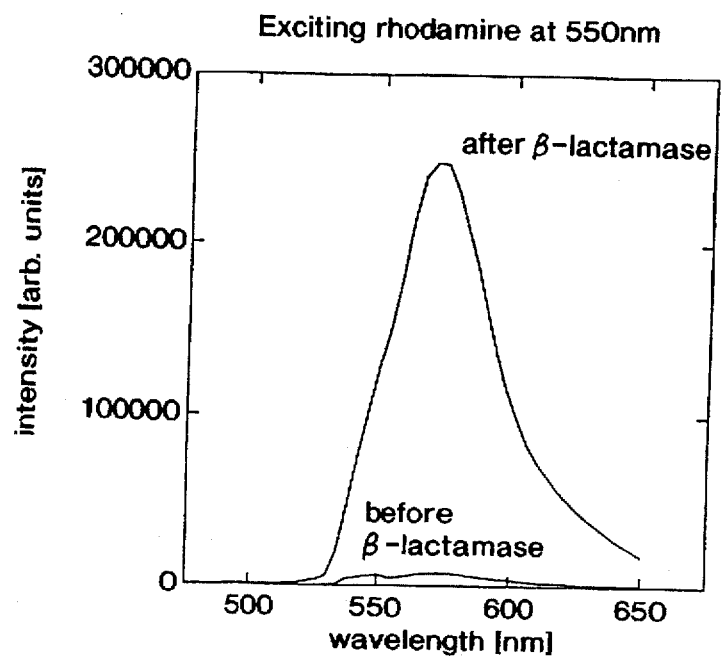
FIGS. 1(a) and 1(b) illustrate the emission spectra for the fluorescein (a) and rhodamine (b) components of compound 11 before and after β-lactamase cleavage of the β-lactam ring.

β-Lactamases are nearly optimal enzymes in respect to their almost diffusion-controlled catalysis of β-lactam hydrolysis [Christensen, H. et al., *Biochem. J.* 266: 853–861 (1990)]. Upon examination of the other properties of this class of enzymes, it was determined that they were suited to the task of an intracellular reporter enzyme. The cleave the β-lactam ring of β-lactam antibiotics, such as penicillins and cephalosporins, generating new charged moieties in the process [O'Callaghan. C. H. et al., *Antimichrob. Agents. Chemother.* 8: 57–63, (1968); Stratton, C. W., *J. Antimicrob. Chemother* 22. Suppl. A: 23–35 (1988)]. A penicillin and a first generation cephalosporin are illustrated with the β-lactam ring in bold type, the arrow pointing to the site of cleavage.

β-Lactamases are a class of enzymes that have been very well characterized because of their clinical relevance in making bacteria resistant to β-lactam antibiotics [Waley, S. G., *Sci. Prog.* 72: 579–597 (1988); Richmond, M. H. et al., *Ann. N.Y Acad. Sci.* 182: 243–257 (1971)]. Most β-lactamases have been cloned and their amino acid sequence determined [see, e.g., Ambler, R. P., *Phil. Trans. R. Soc. Lond.* [*Ser. B.*]289: 321–331 (1980)].

A gene encoding β-lactamase is known to molecular biologists as the ampicillin resistance gene (Amp$^r$) and is commonly used to select for successfully transduced bacteria [Castagnoli, L. et al., *Genet. Res.* 40: 217–231 (1982)]; clones thereof are almost universally available. The enzyme catalyzes the hydrolysis of a β-lactam ring and will not accept peptides or protein substrates [Pratt, R. F. and Govardhan, C. P., *Proc. Natl. Acad. Sci. USA* 81: 1302–1306 (1984); Murphy, B. P. and Pratt, R. F., *Biochemistry* 30: 3640–3649 (1991)]. The kinetics of this reaction is well understood and there is no product inhibition [Bush, K. and Sykes, R. B., *Antimicrob. Agent. Chemother.* 30: 6–10 (1986); Christensen et al. (1990), supra]. The enzyme substrates are less polar than the products. The carboxyl group in the substrate can be easily masked by an acetoxymethyl ester [Jansen, A. B. A. and Russell, T. J., *J. Chem. Soc.* 2127–2132, (1965); Daehne, W. et al., *J. Med. Chem.* 13: 607–612 (1970)], which is readily cleaved by endogenous mammalian intracellular esterases. Conversion by these esterases followed by the β-lactam cleavage by β-lactamase generates two negative charges and a tertiary amine, which protonates. To date, there has been no report of a fluorogenic substrate with the appropriate properties, but multiple chromogenic substrates of different design have been reported and are commercially available [Jones, R. N. et al., *J. Clin. Microbiol.* 15: 677–683 (1982); Jones, R. N. et al., *J. Clin. Microbiol.* 15: 954–958 (1982); O'Callaghan, C. H. et al., *Antimicrob. Agents. Chemother.* 1: 283–288 (1972)].

A large number of β-lactamases have been isolated and characterized, all of which would be suitable for use in accordance with the present invention. Initially, β-lactamases were divided into different classes (I through V) on the basis of their substrate and inhibitor profiles and their molecular weight [Richmond, M. H. and Sykes, R. B., *Adv. Microb. Physiol.* 9: 31–88 (1973)]. More recently, a classification system based on amino acid and nucleotide sequence has been introduced [Ambler, R. P., *Phil. Trans. R. Soc. Lond.* [*Ser.B.*]289: 321–331 (1980)]. Class A β-lactamases possess a serine in the active site and have an approximate weight of 29 kd. This class contains the plasmid-mediated TEM β-lactamases such as the RTEM enzyme of pBR322. Class B β-lactamases have an active-site zinc bound to a cysteine residue. Class C enzymes have an active site serine and a molecular weight of approximately 39 kd, but have no amino acid homology to the class A enzymes.

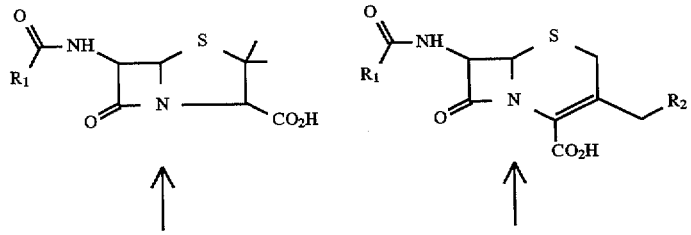

The coding region of an exemplary β-lactamase employed in the reporter gene assays described herein is indicated in SEQ ID NO:1 (nucleic acid sequence) and SEQ ID NO:2 (amino acid sequence). The pTG2del1 containing this sequence has been described [Kadonaga, J. T. et al., *J. Biol. Chem.* 259: 2149–2154 (1984)]. The entire coding sequence of wildtype pBR322 β-lactamase has also been published

[Sutcliffe, J. G., *Proc. Natl. Acad. Sci. USA* 75: 3737–3741 (1978)]. As would be readily apparent to those skilled in the field, this and other comparable sequences for peptides having β-lactamase activity would be equally suitable for use in accordance with the present invention. The g-lactamase reporter gene is employed in an assay system in a manner well known per se for the use of reporter genes (for example, in the form of a suitable plasmid vector).

In conjunction with a suitable β-lactamase, there are employed in accordance with the present invention fluorogenic substrates of the general formula I

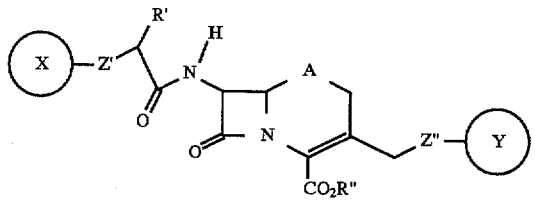

in which one of X and Y is a fluorescent donor moiety and the other is a quencher (which may or may not re-emit); R' is selected from the group consisting of H, lower alkyl and $(CF_2)_nOH$, in which n is 0 or an integer from 1 to 5; R" is selected from the group consisting of H, physiologically acceptable metal and ammonium cations, $—CHR^2OCO(CH_2)_nCH_3$, $—CHR^2OCOC(CH_3)_3$, acylthiomethyl, acyloxy-alpha-benzyl, delta-butyrolactonyl, methoxycarbonyloxymethyl, phenyl, methylsulphinyhmethyl, beta-morpholinoethyl, dialkylaminoethyl, acyloxyalkyl, dialkylaminocarbonyloxymethyl and aliphatic, in which $R^2$ is selected from the group consisting of H and lower alkyl; A is selected from the group consisting of S, O, SO, $SO_2$ and $CH_2$; and Z' and Z" are linkers for the fluorescent donor and quencher moieties.

The linkers Z' and Z" serve the purpose of attaching the fluorescent donor and quencher moieties to the cephalosporin-derived backbone, and may facilitate the synthesis of the compounds of general formula I. In general formula I, Z' may represent a direct bond to the backbone; alternatively, suitable linkers for use as Z' include, but are not limited to, the following: $—(CH_2)_nCONR^2(CH_2)_m—$, $—(CH_2)_nNR^2CO(CH_2)_m—$, $—(CH_2)_nNR^3CONR^2(CH_2)_m—$, $—(CH_2)_nNR^3CSNR^2(CH_2)_m—$, $—(CH_2)_nCONR^3(CH_2)_pCONR^2(CH_2)_m—$, $—(CH_2)_n—$, $—(CH_2)_nNR^3CO(CH_2)_pS(CH_2)_{2m}—$, $—(CH_2)_nS(CH_2)_m—$, $—(CH_2)_nO(CH_2)_m—$, $—(CH_2)_nNR^2(CH_2)_m—$, $—(CH_2)_nSO^2NR^2(CH_2)_m—$, $—(CH_2)_nCO^2(CH_2)_m—$,

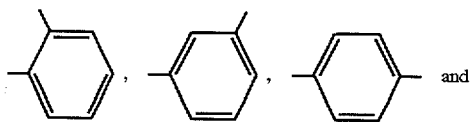 and

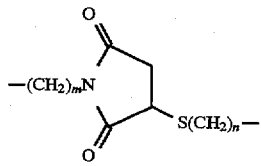

wherein $R^2$ and n are as previously defined; $R^3$ is selected from the group consisting of hydrogen and lower alkyl; and each of m and p is independently selected from the group consisting of 0 and integers from 1 to 4. Suitable linkers Z" for the Y moiety include, but are not limited to, a direct bond to a heteroatom (e.g., O, N or S) in the dye's chromophore or the following: $—O(CH_2)_n—$, $—S(CH_2)_n—$, $—NR^2(CH_2)_n—$, $—N^+R^2{}_2(CH_2)_n—$, $—OCONR^2(CH_2)_n—$, $—O_2C(CH_2)_n—$, $—SCSNR^2(CH_2)_n—$, $—SCSO(CH_2)_n—$, $—S(CH_2)_nCONR^2(CH_2)_m$, $—S(CH_2)_nNR^2CO(CH_2)_m$, and

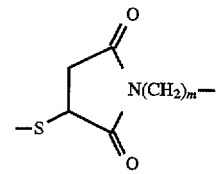

in which $R^2$, n and m are as previously defined.

As would readily be appreciated by those skilled in the art, the efficiency of fluorescence resonance energy transfer depends on the fluorescence quantum yield of the donor fluorophore, the donor-acceptor distance and the overlap integral of donor fluorescence emission and acceptor absorption. The energy transfer is most efficient when a donor fluorophore with high fluorescence quantum yield (preferably, one approaching 100%) is paired with an acceptor with a large extinction coefficient at wavelengths coinciding with the emission of the donor. The dependence of fluorescence energy transfer on the above parameters has been reported [Forster, T. (1948) *Ann. Physik* 2: 55–75; Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, Vol 30, ed. Taylor, D. L. & Wang, Y. -L., San Diego: Academic Press (1989), pp. 219–243; Turro, N. J., *Modern Molecular Photochemistry*, Menlo Part: Benjamin/Cummings Publishing Co., Inc. (1978), pp. 296–361], and tables of spectral overlap integrals are readily available to those working in the field [for example, Berlman, I. B. *Energy transfer parameters of aromatic compounds*, Academic Press, New York and London (1973)]. The distance between donor fluorophore and acceptor dye at which fluorescence resonance energy transfer (FRET) occurs with 50% efficiency is termed $R_0$ and can be calculated from the spectral overlap integrals. For the donor-acceptor pair fluorescein-tetramethyl rhodamine which is frequently used for distance measurement in proteins, this distance $R_0$ is around 50–70 Å [dos Reimdios, C. G. et al. (1987) *J. Muscle Research and Cell Molility* 8:97–117]. The distance at which the energy transfer in this pair exceeds 90% is about 45 Å. When attached to the cephalosporin backbone the distances between donors and acceptors are in the range of 10 Å to 20 Å, depending on the linkers used and the size of the dyes. For a distance of 20 Å, a dye pair will have to have a calculated $R_0$ of larger than 30 Å for 90% of the donors to transfer their energy to the acceptor, resulting in better than 90% quenching of the donor fluorescence. Cleavage of such a cephalosporin by β-lactamase relieves quenching and produces an increase in donor fluorescence efficiency in excess of tenfold. Accordingly, it is apparent that identification of appropriate donor-acceptor pairs for use as taught herein in accordance with the present invention would be essentially routine to one skilled in the art.

To measure β-lactamase activity in the cytoplasm of living cells, smaller molecular weight dyes as hereinafter described are in general preferred over larger ones as substrate delivery becomes a problem for larger molecules. Large molecules also tend to bind more avidly to cellular constituents than small ones, thereby removing at least some of them from access and cleavage by β-lactamase.

Fluorescent dyes suitable for use as X and Y are well known to those skilled in the art. Generic structures of particular classes of fluorescent dyes suitable for use as X and Y are provided below. Compounds of general formulas II–XXXIV are exemplary of dyes which serve as the basis for particularly suitable donor moieties in the compounds of general formula I. Suitable acceptor dyes for use as the basis of acceptor moieties in the compounds of general formula include, but are not limited to, compounds of general formulas II–LIV.

Coumarins and related dyes

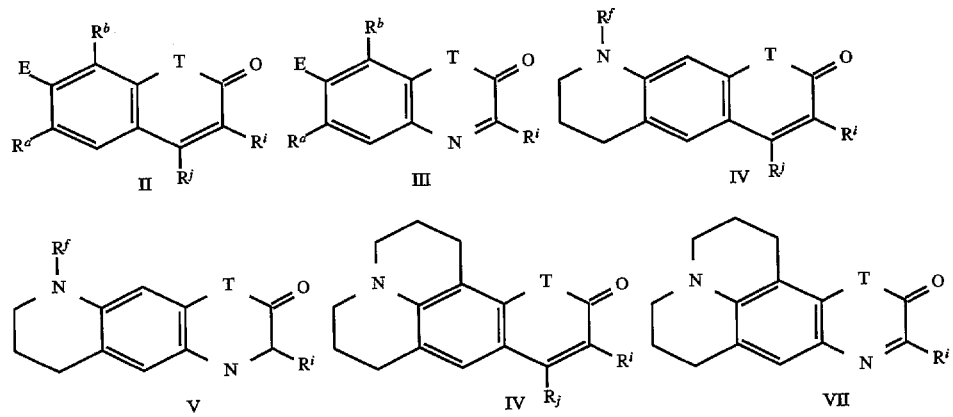

Xanthene dyes (including fluoresceins, rhodols and rhodamines)

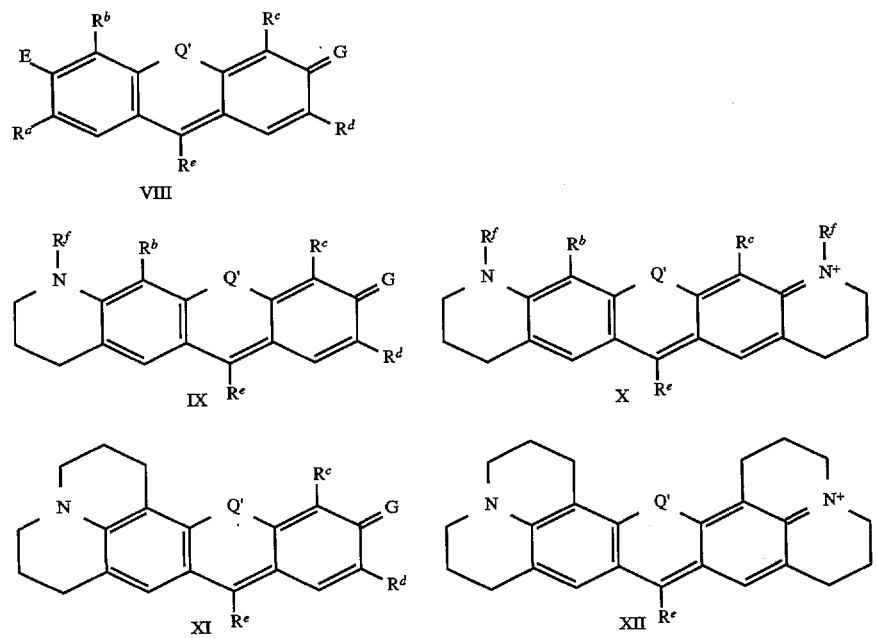

Resorufins

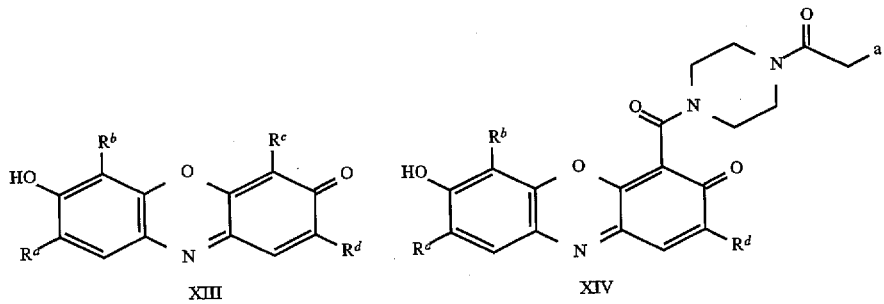

Cyanine dyes
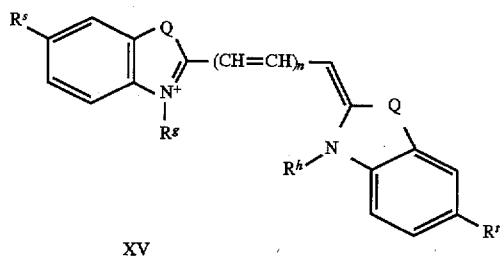
XV
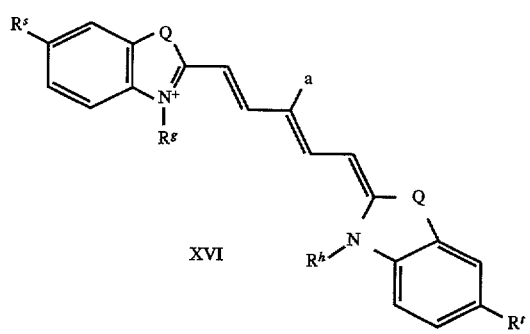
XVI
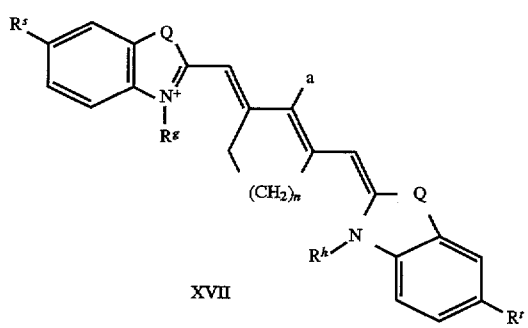
XVII
Difluoroboradiazaindacene dyes
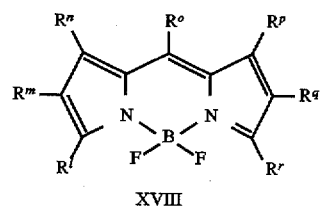
XVIII
Bimanes
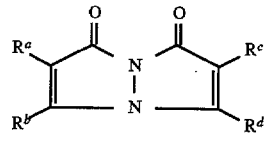
XIX
Acridines
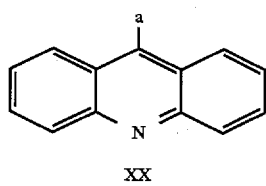
XX
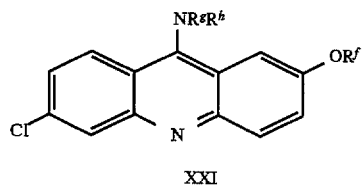
XXI
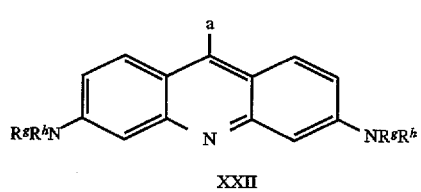
XXII
Isoindoles
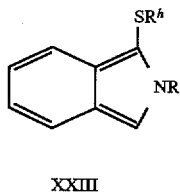
XXIII
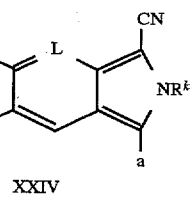
XXIV
Dansyl dyes
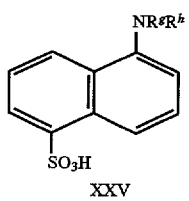
XXV
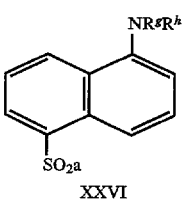
XXVI Aminophthalic hydrazides (luminol and isoluminol derivatives) Aminophthalimides

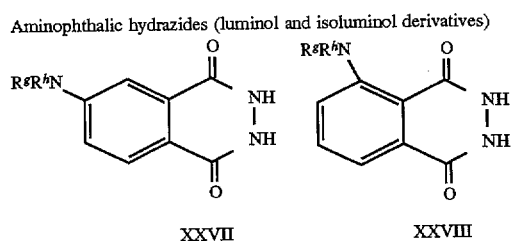

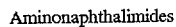     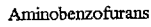     
XXVII         XXVIII         XXIX         XXX Aminonaphthalimides     Aminobenzofurans     Aminoquinolines

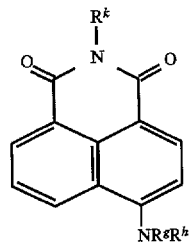     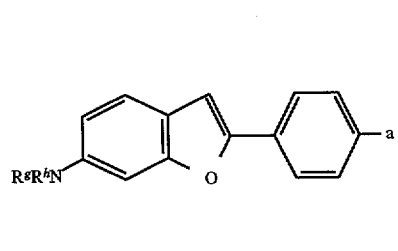     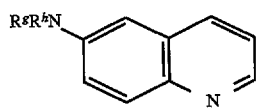

XXXI         XXXII         XXXIII

Dicyanohydroquinones     Indigo Dyes     Anthraquinone dyes

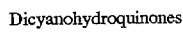     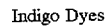     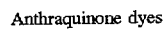

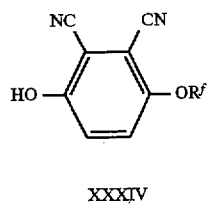     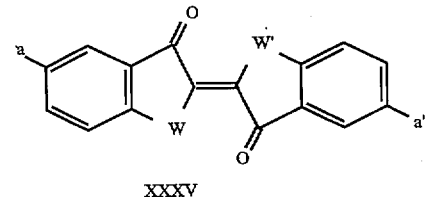     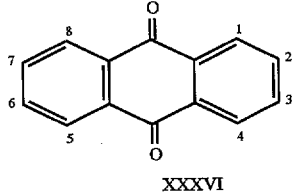

XXXIV         XXXV         XXXVI

Polymethine dyes

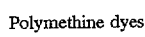

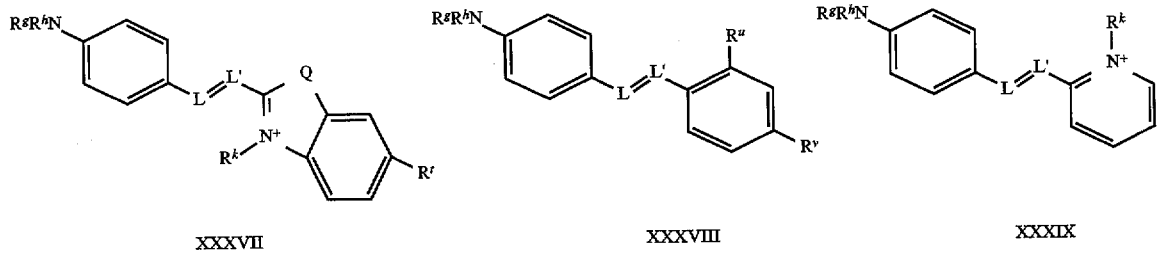

XXXVII         XXXVIII         XXXIX

Nitro dyes and cyano derivatives

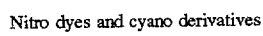

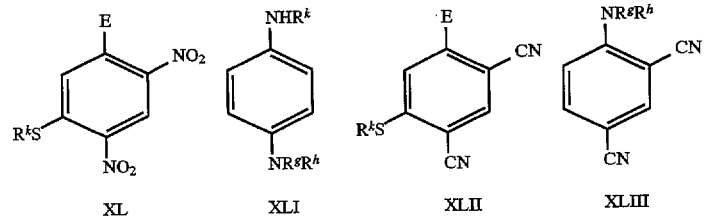

XL         XLI         XLII         XLIII

Quinone dyes

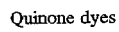

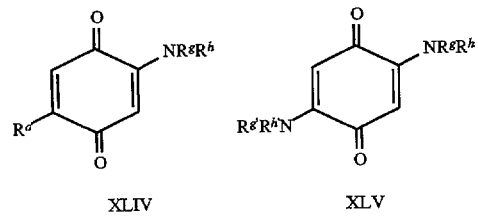

XLIV         XLV

Xanthene dyes

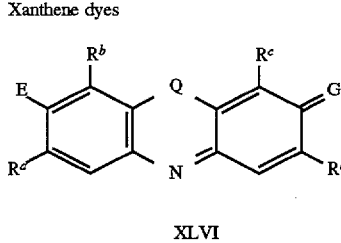
XLVI

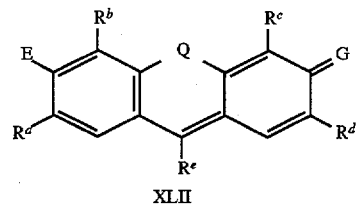
XLII

Dicyanovinyl and tricyanovinyl dyes

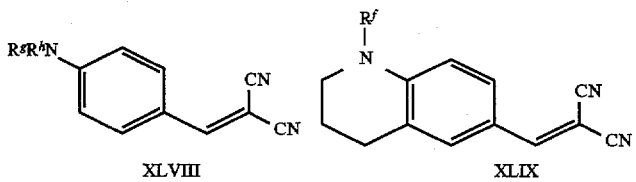
XLVIII     XLIX

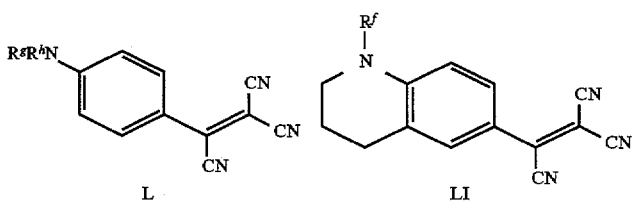
L     LI

Indoaniline dyes (ninhydrin derivatives)

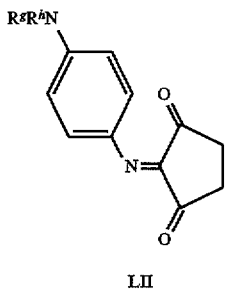
LII

Di- and triphenylmethane dyes

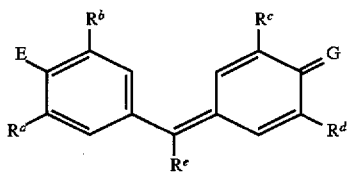
LIII

Indamines and related dyes

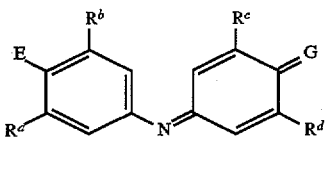
LIV

In preferred embodiments of the compounds of general formulas II–LIV:

- each of a and a' is independently H or an attachment point (i.e., a location at which the dye moiety is attached to the core structure of general formula I;
- E is selected from the group consisting of H, OH, $OR^k$ and $NR^gR^h$;
- G is selected from the group consisting of O and $N^+R^gR^h$;
- each of L and L' is independently selected from the group consisting of CH and N;
- Q is selected from the group consisting of O, S, $C(CH_3)_2$; and $NR^g$;
- Q' is selected from the group consisting of O, $CH_2$, $C(CH_3)_2$, $NR^k$ and $SO_2$;
- T is selected from the group consisting of O and $NR^k$;
- each of W and W' is selected from the group consisting of O, S, Se and NH:
- each of $R^a$, $R^b$, $R^c$ and $R^d$ is independently selected from the group consisting of an attachment point, H, halogen and lower alkyl;
- $R^c$ is selected from the group consisting of an attachment point, H, lower alkyl, $CH_2(CH_2)_nCO_2H$, $CH_2(CH_2)_nCH_2CO_2H$, $CH_2(CH_2)_nCO_2a$,

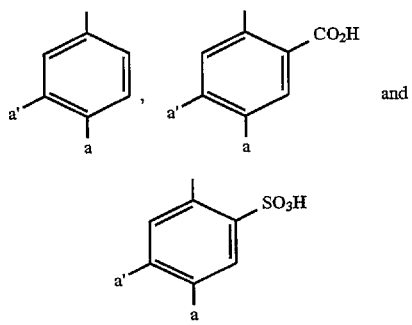

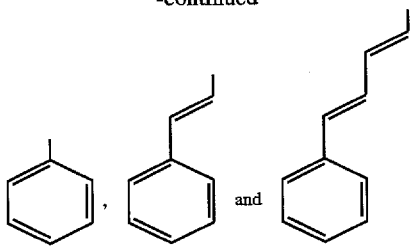

each of $R^r$, $R^s$, $R^{s'}$, $R^h$, $R^{h'}$ and $R^k$ is independently selected from the group consisting of an attachment point, H, lower alkyl and $CH_2(CH_2)_n a$;

$R^j$ is selected from the group consisting of an attachment point, H, halogen, lower alkyl, CN, $CF_3$, phenyl, $CO_2H$ and $CONR^{g'}R^{h'}$;

$R^i$ is selected from the group consisting of an attachment point, H, halogen, lower alkyl, CN, $CF_3$, phenyl, $CH_2CO_2H$, $CH_2CONR^{g'}R^{h'}$;

each of $R^t$ and $R^r$ is independently selected from the group consisting of an attachment point, H, lower alkyl, each of $R^m$, $R^n$, $R^p$ and $R^q$ is independently selected from the group consisting of an attachment point, H, lower alkyl and phenyl;

$R^o$ is selected from the group consisting of an attachment point, H and lower alkyl;

each of $R^s$ and $R^t$ is independently selected from the group consisting of an attachment point, H, halogen, lower alkyl and $OR^r$;

each of $R^u$ and $R^v$ is independently selected from the group consisting of an attachment point, H, halogen, CN and $NO_2$;

and n is as previously defined. In the anthraquinone dyes of general formula XXXIX, each of positions 1–8 may carry a substituent H or E, or serve as an attachment point.

A general method for synthesis of compounds of general formula I is depicted below.

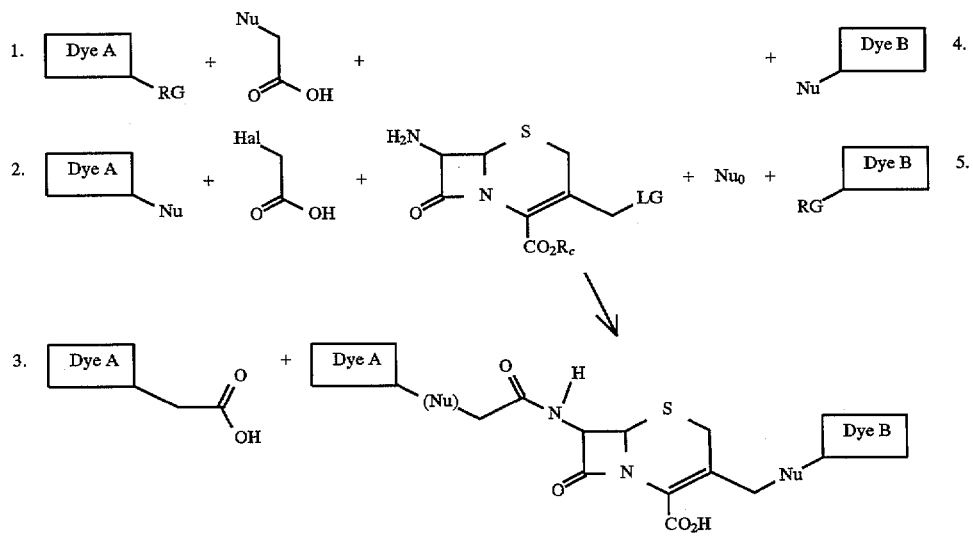

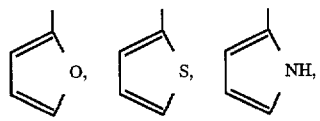

In these compounds, RG is a nucleophile-reactive group (e.g., iodoacetamide, isocyanate, isothiocyanate, etc.); Nu is a nucleophile (e.g., —SH, —$NH_2$, —OH, etc.); $R_0$ is H or an ester group (e.g., benzhydryl ester, tertiary butyl ester, etc.); $Nu_0$ is a bidentate nucleophile (e.g., HS, $HSCH_2CH_2NH_2$, xanthate, etc.); and Hal is a halogen (e.g., chlorine, bromine or iodine).

The cephalosporin starting materials are commercially available cephalosporin derivatives 7-aminocephalosporanic acid or 7-amino 3'-chlorocephalosporanic acid as its benzhydryl or tertiary butyl ester ($R_0$). Prior to coupling the dyes A and B carrying nucleophile reactive groups (RG) it is sometimes advantageous to esterify or alkylate their phenolic and free amine residues. The order of attaching dye A and dye B depends on the choice of reagents. Dye A is tethered to the cephalosporin via an alkyl amide linker. This is achieved by reacting a dye A carrying a nucleophile-reactive group (RG) with a nucleophilic alkyl acid (e.g., amino-, mercapto- or hydroxyalkyl acid) and coupling of the acid to the cephalosporin 7-amine (path 1). Alternatively, dye A carrying a nucleophilic group (e.g., amine or thiol) is reacted with a halogenated alkyl acid coupled to the cephalosporin 7-amine (path 2). In both pathways, the order of the two reactions can be reversed. Dyes A containing an aliphatic acid can be directly coupled to the cephalosporin (path 3). Dye B carrying a nucleophilic substituent can be coupled to the 3'-position in the cephalosporin by direct displacement of the leaving group (LG) (path 4). A Dye B carrying a nucleophile-reactive group can be reacted with a bidentate nucleophile which is coupled then attached to the cephalosporin by leaving group (LG) displacement (path 5); the order of the reactions can be reversed. In some cases it might be necessary to conduct the first reaction with a bidentate nucleophile with one of its nucleophilic groups masked. The second coupling is then performed after removal of that protection group. After attachment of both dyes the cephalosporin ester is cleaved (in cases where $R_o$ is not H). To make membrane permeant substrates the acid is then re-esterified to esters that can be deprotected by the cytoplasmic environment of a mammalian cell. For applications not involving cell cytoplasm, any remaining acyl and alkyl groups that were used to mask phenols and free amines on the dyes are removed.

Preferred combinations of classes of donors and acceptors suitable for use in accordance with the present invention are indicated in Table 1. In embodiments of compounds of general formula I using these combinations, fluorescent resonant energy transfer (FRET) occurs. Of course, as would be readily understood by those working in the field, many other combinations of donors and acceptors (including those that re-emit and those that do not) would be suitable for use in accordance with the present invention.

TABLE 1

| ACCEPTORS | DONORS | | |
|---|---|---|---|
| | II–VIII, XIX–XXI, XXIII–XXXIV | VII–XIV, XVII XXII | XV–XVII |
| II–VIII, XIX–XXI, XXIII–XXXIV | FRET | | |
| VII–XIV, XVII, XXII | FRET | FRET | |
| XV–XVII | FRET | FRET | FRET |
| XL–XLV, XLVII–LII | FRET | FRET | |
| XXXV–XXXIX, XLVI–XLVII, LIII–LIV | FRET | FREI | FRET |

Fluorescent donor moieties of particular interest include coumarins and fluoresceins. Particular quenchers of interest include fluoresceins, rhodols and rhodamines. Combinations of interest include the use of a coumarin donor with a fluorescein, rhodol or rhodamine quencher, and a fluorescein donor with a rhodol or rhodamine quencher. Specific combinations of interest include the following: a coumarin (e.g., 7-hydroxycoumarin) or chloro derivative thereof with a fluorescein or dichloro derivative thereof; a fluorescein with an eosin or tetrachlorofluorescein; a fluorescein with a rhodol derivative; and a rhodamine with a fluorescein.

In general, it is desirable that the compounds of general formula I are membrane-permeant fluorogenic precursors. Therefore, it is preferred that any phenolic hydroxyls or free amines in the dye structures are either acylated with $C_1-C_4$ acyl groups (e.g., acetyl) or converted to various other esters and carbonates [for example, as described in Bundgaard, H., *Design of Prodrugs*, Elsevier Science Publishers (1985), Chapter 1, page 3 et seq.]. Phenols can also be alkylated with alkyloxy alkyl groups (e.g., such groups as are identified as suitable for use as R" in general formula I). In the case of fluoresceins, rhodols and rhodamines this manipulation is particularly useful, as it also results in conversion of the acid moiety in these dyes to the spirolactone.

The cephalosporin backbone serves as a cleavable linker between two dyes. After cleavage it provides the charges necessary to keep one of the two dyes inside the cell. Dyes are chosen in a manner that one dye absorbs light (quencher or acceptor chromophore) at the wavelength that the other one emits (donor fluorophore). In the intact cephalosporin the two dyes are in close proximity to each other. When exciting the fluorophore one observes fluorescence resonance energy transfer (FRET) from the donor to the acceptor instead of donor fluorescence [Forster, T., *Ann. Physik* 2: 55–75 (1948)]. If the acceptor is a nonfluorescent dye the energy is given off to the solvent; the donor fluorescence is quenched. In the case of the acceptor being itself a fluorescent dye, fluorescence re-emission occurs at the acceptor's emission wavelength. In polar solvents such as water, hydrophobic donor and acceptor fluorophores can stack when separated by a short flexible linker. Due to this association in the ground state, a "dark complex" is formed [Yaron, A. et al., *Anal. Biochem.* 95: 228–235 (1979)]. In this complex, neither fluorophore can emit light, causing the fluorescence of both dyes to be quenched [Bojarski, C. and Sienicki, K. Energy transfer and migration in fluorescent solutions. In: *Photochemistry and Photophysics*, edited by Rabek, J. F. Boca Raton: CRC Press, Inc., 1990, pp. 1–57]. In either case, a large change in fluorescence goes along with β-lactam cleavage, which can be used to measure β-lactamase activity. As both dyes diffuse away from each other, stacking and energy transfer are disrupted. Cephalosporins carrying a donor and an acceptor dye which fluoresces are referred to herein as FRET-cephalosporins.

Fluorescence resonance energy transfer has been used as a spectroscopic ruler for measuring molecular distances in proteins and peptides as it is effective in the range from 10–100 Å. This energy transfer is proportional to the inverse sixth power of the distance between donor and acceptor. Its efficiency is higher, the better donor emission and acceptor absorbance overlap, and the longer the fluorescence lifetime of the donor (in absence of the acceptor). FRET can be very efficient over distances of 10–20 Å.

In the cephalosporin, distances for attachment of donor and acceptor are greater than 10 Å and a minimum of 10 bond-lengths, if one includes the two minimal spacers at 7- and 3-positions. Over this distance FRET is very efficient, if the right donor-acceptor pairs are chosen. Conveniently, in a FRET-cephalosporin the 7-amine tethered dye stays attached to the polar hydrolysis products of cephalosporin cleavage, trapping it in the cells' cytoplasm. This position is best occupied by the donor fluorophore, although in some instances the acceptor may occupy this position. Upon cleavage, fluorescence increases due to loss of the quencher dye.

The acceptor fluorophore is generally attached by a linker which imparts the greatest stability of the substrate to nucleophilic attack. A preferred linker is a thioether bond (—S—), which is very stable and due to its inductive effect reduces the reactivity of the β-lactam ring toward nucleophiles [Page, M. I., Adv. Phys. Org. Chem. 23: 165–270 (1987)]. In addition, the free thiol or thiolate group released upon hydrolysis often quenches the attached fluorophore, adding to the desired large change in fluorescence upon hydrolysis.

The fluorogenic substrates of the invention are initially colorless and nonfluorescent outside cells. The substrates are designed so they readily cross cell membranes into the cytoplasm, where they are converted to fluorescent compounds by endogenous nonspecific esterases and stay trapped due to their charges. In the intact molecules, fluorescence energy transfer occurs leading to fluorescence at a particular wavelength when the substrates are excited. Lactamase cleavage of the β-lactam ring is followed by expulsion of the fluorescein moiety with loss of fluorescence energy transfer. Excitation of the modified substrate now results in fluorescence at a different wavelength.

The assay systems of the present invention make use of highly fluorescent dyes attached to the cephalosporin backbone, the fluorescence of which is so intense that the dyes can be readily detected in solution at sub-nonmolar concentrations. Cleavage of the cephalosporin backbone is detected by a change in fluorescence color and no further processing is necessary. Thus, the present invention provides significant advantages relative to prior art assays described in the prior art, such as in U.S. Pat. No. 4,740,459 (the entire disclosure of which is hereby incorporated by reference). In the assay of U.S. Pat. No. 4,740,459, for example, weakly fluorescent β-lactamase conversion products of commercial β-lactam antibiotics are detected only after heating a drop of solution containing same on filter paper and examining the products with a UV lamp.

As would be immediately apparent to those working in the field, the combination of a novel substrate in accordance with the invention and a suitable β-lactamase may be employed in a wide variety of different assay systems (such as are described in U.S. Pat. No. 4,740,459). In particular, the fluorogenic substrates of the invention enable the detection of β-lactamase activity in a wide variety of biologically important environments, such as human blood serum, the cytoplasm of cells and intracellular compartments; this facilitates the measurement of periplasmic or secreted β-lactamase.

Further, the expression of any target protein can be detected by fusing a gene encoding the target protein to a β-lactamase gene, which can be localized by immunostaining and fluorescence or electron microscopy. For example, β-lactamase fusion proteins may be detected in the lumen of organelles through the use of the substrates of the invention; only subcellular compartments containing the fusion protein fluoresce at a wavelength characteristic of the cleaved substrate, whereas all others fluoresce at a wavelength characteristic of the intact molecule.

Both the intact and cleaved substrate are well retained in cells without the use of special measures, such as chilling. The color change (even in individual small mammalian cells) is visible through a fluorescence microscope using normal color vision or photographic film; the fluorescence signal may be quantified and further enhanced by conventional digital image processing techniques. Moreover, because gene activation is detected not by a change in a single intensity but rather by a color change or a change in the ratio between two intensities at different wavelengths, the assays of the present invention are relatively immune to many artifacts such as variable leakiness of cells, quantity of substrate, illumination intensity, absolute sensitivity of detection and bleaching of the dyes.

In addition, the presence (for example, in human serum, pus or urine) of bacteria resistant to β-lactam antibiotics can be readily detected using the substrates of the present invention. Only in the presence of an active β-lactamase is there a change in the fluorescence spectrum from that of the intact molecule to one characteristic of the cleavage product. The substrates of the present invention are superior to prior art chromogenic substrates Nitrocephin and PADAC, in that the inventive substrates are stable to human serum. The novel substrates are also more sensitive than the chromogenic substrate CENTA, because they experience a much smaller optical background signal from human serum and a lower detection limit for fluorescence versus absorbance.

A variety of substrates (e.g., compounds of general formulas 17, 22 and 25) have been prepared and their emission spectra obtained before and after β-lactamase cleavage. These substrates allow for β-lactamase detection primarily in vitro, as they bind strongly to serum and cellular proteins. Due to their hydrophobic nature, the fluorophores stack; this leads to a loss of fluorescence in the intact substrate. β-lactamase cleaves the substrates and relieves the stacking, allowing for fluorescence. Compounds (e.g., 11) with reversed location of donor and acceptor fluorophore on the cephalosporin exhibit similar fluorescence behavior.

In one preferred embodiment of the invention, a compound of general formula 1 was coupled to a compound of general formula 2 to form a compound of general formula 3. Commercially-available compound 4 was then coupled to compound 3 using dicyclohexylcarbodiimide and the product reacted with compound 5, yielding a compound of general formula 6. Deprotection of compound 6 generated a compound of general formula 7. In exemplary embodiments, Acyl was acetyl, $R^x$ was Me and $R^yH$ (a), or Acyl was butyryl, $R^x$ was H and $R^yCl$ (b); $R^7$ was trimethylsilyl or benzyl.

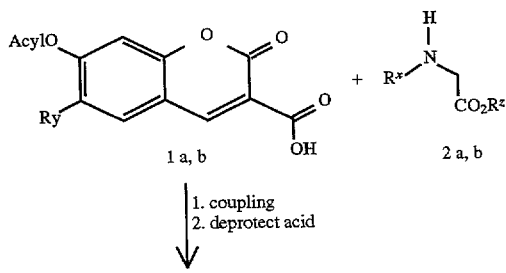

21

-continued

22

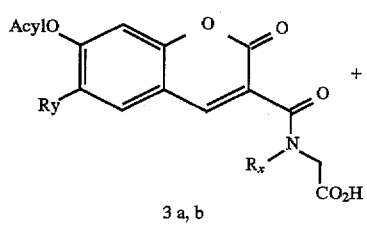
3 a, b

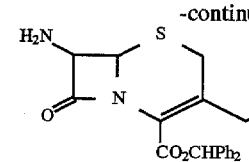
4

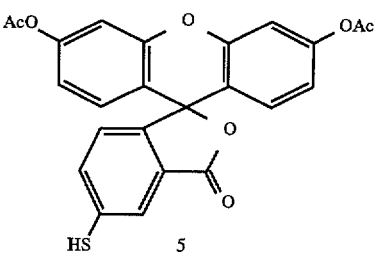
5

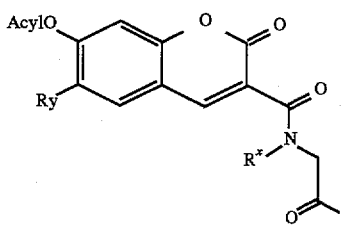

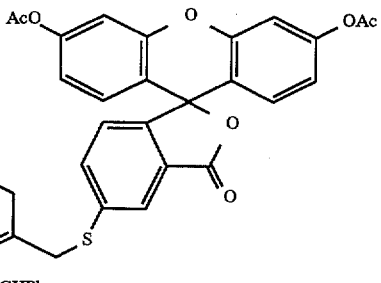
6 a, b

↓ deprotect

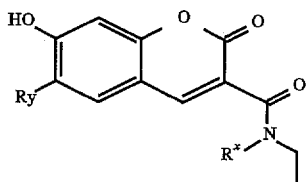
7 a, b

The compounds of general formula 6 were modified to obtain membrane permeant derivatives which were converted to the corresponding fluorescent compounds of general formula 7 in intact cells due to the action of endogenous nonspecific esterases. In these molecules, fluorescence resonance energy transfer occurs from the 7-hydroxycoumarin moiety to the fluorescein moiety, leading to green fluorescence when the compounds are excited at about 400 nm. After cleavage of the β-lactam ring, excitation of the 7-hydroxycoumarin moiety results in blue fluorescence; in exemplary embodiments, a 25-fold increase in fluorescence at about 450 nm and a three-to fourfold decrease in fluorescence at 515 nm was observed.

The invention may be better understood with reference to the accompanying examples, which are intended for purposes of illustration only and should not be construed as in any sense limiting the scope of the invention as defined in the claims appended hereto.

EXAMPLES

All silica gel chromatography was performed using silica gel (Merck, grade 60, 230–400 mesh, 60 Å) purchased from Aldrich. Bakerbond Octadecyl from J. T. Baker was used for $C_{18}$ reverse phase chromatography. Solvents (high pressure liquid chromatography grade) were used for chromatography as received, or dried over activated molecular sieves (3 Å) for synthetic purposes.

Fluorescence excitation and emission spectra were measured either on a Spex Fluorolog 111 or on a K2 fluorometer (ISS, Champaigne, Ill.) in ratio mode with a rhodamine B quantum counter. The efficiency of fluorescence energy transfer was determined from the change in the integrated fluorescence emission at the donor emission wavelength upon treatment with β-lactamase. For fluorescence microscopy imaging, two different imaging setups were used. One, with an inverted fluorescence microscope, Zeiss IM-35 (Thornwood, N.Y.) coupled to a silicon-intensified target (SIT) camera (Dage-MTI, Michigan City, Ind.) has been described in detail [Tsien, R. Y. (1986) New tetracarboxylate chelators for fluorescence measurement and photochemical manipulation of cytosolic free calcium concentrations, in: *Optical Methods in Cell Physiology*, ed. de Weer, P. & Salzberg, B., New York: Wiley, pp. 327–345; Tsien and Harootunian (1990) *Cell Calcium* 11:93–109]. The other consisted of a cooled charge-coupled-device (CCD) camera (Photometrics, Tucson, Ariz.) connected to an inverted fluorescence microscope (Zeiss Axiovert).

Fluorescence resonance energy transfer was measured by monitoring the ratio of fluorescence intensities at donor and acceptor emission wavelengths using commercially-available filters (Omega Optical).

Excitation: 360 DF 40, dichroic mirror 390 DCLP or 405 DF 15, dichroic mirror 420 DRLPO2

Emission: 450 DF 65 (donor emission) 515 EFLP (acceptor emission) 435 EFLP (to view donor and acceptor fluorescence simultaneously)

Example 1 (Compound 11)

To test the optical properties of a cephalosporin with two dye molecules attached the following model compound was synthesized.

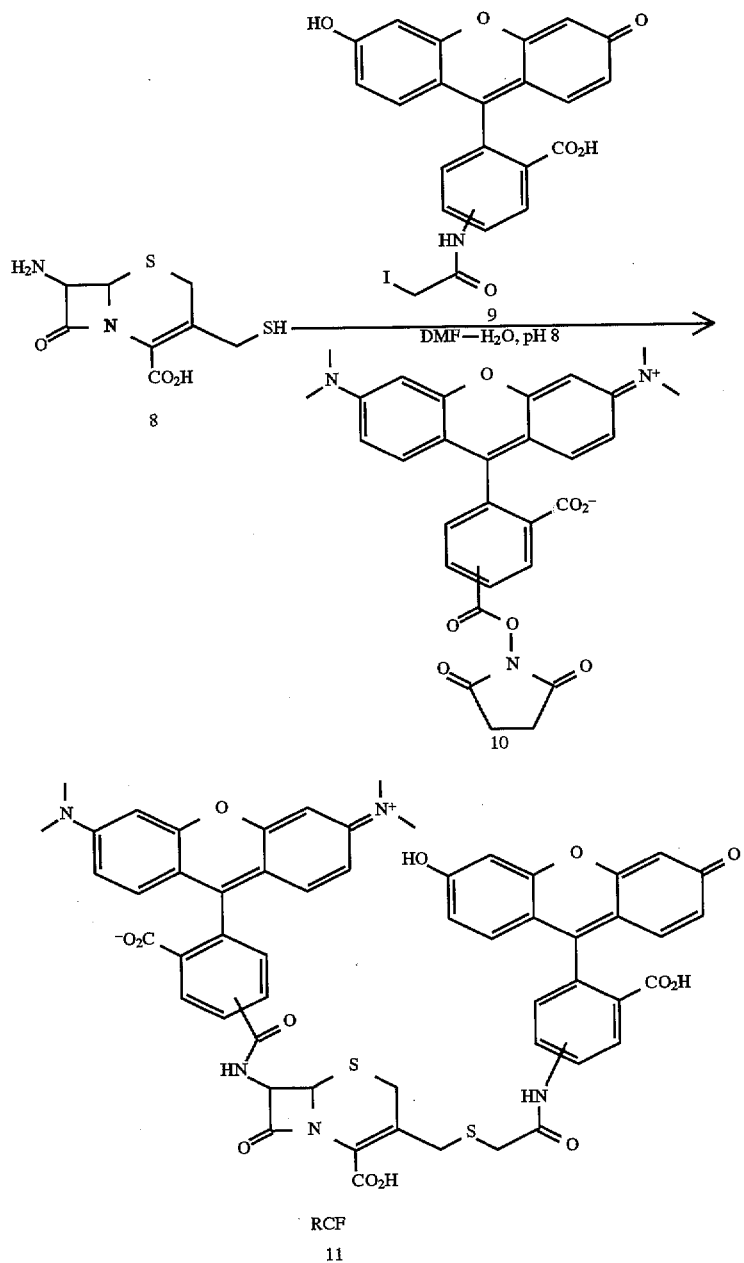

The first synthesis step was to convert 7-aminocephalosporanic acid into a bifunctional cephalosporin carrying a thiol in the 3'-position and the 7-amine [Van Heyningen, E. and Brown, C. N., *J. Med. Chem.* 8: 174–181 (1965); Japanese Patent, Kokai 75/18494, CA 85, 9732d]. This cephalosporin was then reacted selectively with an thiol-reactive dye, followed by an amine-reactive dye. The thiol-reactive dye 5,(6)-icodoacetamidofluorescein and the amine-reactive dye 5,(6)-carboxy-N,N,N',N'-tetramethylrhodaminesuccinimide were coupled to the cephalosporin in aqueous dimethylformamide at pH 8. The product will be referred to as RCF.

Figure 1B:
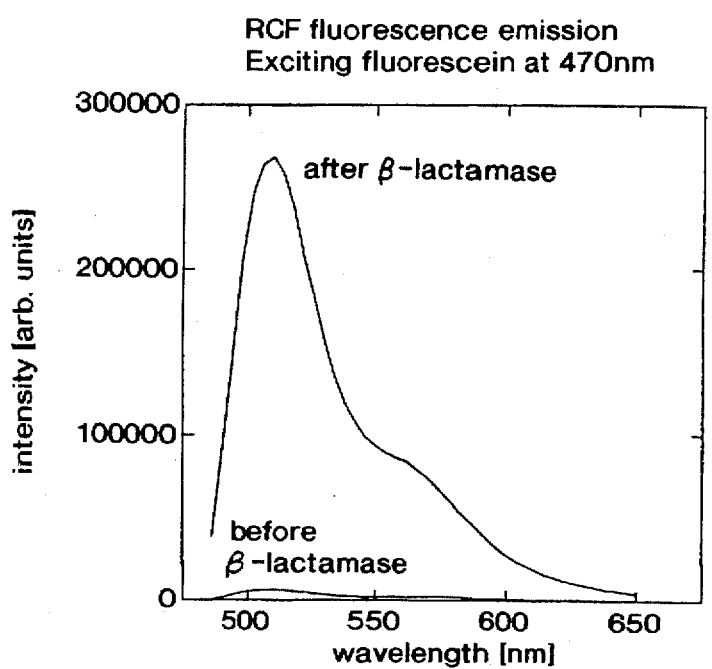

In phosphate buffer at pH 7 RCF is virtually non fluorescent; neither fluorescein nor rhodamine show much fluorescence when excited at their respective excitation maxima. which is indicative of chromophore stacking ("dark complex"). After long term treatment with β-lactamase the β-lactam is cleaved causing the fluorescence of both dyes to reappear (FIGS. 1(a) and 1(b)). This experiment confirms that one can measure β-lactamase catalyzed hydrolysis of the β-lactam in cephalosporins by the loss of fluorescence quenching using an appropriate donor-acceptor pair.

Example 2

The thiomethyl linker was introduced by conversion of 5-fluoresceinamine to 5-mercapofluorescein via diazotization, conversion to the ethylxanthate, and degradation of the xanthate by aqueous acid to the free sulfhydryl. It was coupled to 7-bromoacetamido-cephalosporanic acid by nucleophilic displacement of the bromide by the mercapto group of the fluorescein. 7-Bromoacetamidocephalosporanic acid had been prepared from 7-aminocephalosporanic acid and bromoacetyl bromide [Bunnell, C.A. et al. Industrial manufacture of cephalosporins. In: Beta-Lactam *Antibiotics for Clinical Use. Series: Clinical Pharamacology*. Vol. 4, edited by Queener, S. F., Webber, J. A. and Queener, S. W. New York: M. Dekker, 1986, p. 255–283].

To prepare 7β-[(5-diacetylfluoroscein)thio]acetamido-3-(acetoxymethyl)-3-cephem-4-carboxylic acid (14), in a nitrogen atmosphere 130 mg (0.29 mmol) 5-fluoresceinthiol diacetate were dissolved in 10 ml dimethylformamide and added to 120 mg (0.31 mmol) 7β-bromoacetamido-3-(acetoxymethyl)-3-cephem-4-carboxylic acid in 10 ml 1M potassium phosphate buffer adjusted to pH 8.0. The solution was stirred for 8 hours at room temperature after which the solvents were removed in vacuo. The residue was dissolved in 10 ml water and the pH of the solution was carefully adjusted to pH 5 with dilute phosphoric acid. At this point nonpolar byproducts precipitated and were removed by centrifugation. Further acidification to pH 2.7 precipitated the title compound which was collected by centrifugation, washed 3 times with 2 ml diethylether-tetrachloromethane (1:2), and dried in vacuo. $^1$H NMR (CDCl$_3$): δ 2.08 ppm (s, 3H, acetate), δ 3.36 ppm, 3.53 ppm (2d, 2H, J=17.3 Hz, C-2), δ 3.87 ppm (s, 2H, side chain methylene), δ 4.88 ppm, 5.16 ppm (2d, 2H, J=13.6 Hz, C-3'), δ 4.96 ppm (d, 1H, J=4.9 Hz, C-6), δ 5.81 ppm (dd, 1H, J$_1$=8.2 Hz, J$_2$=4.9 Hz, C-7), δ 6.85 ppm (m, 4H, xanthene), δ 7.10 (s, 2H, xanthene), δ 7.15 ppm (d, 1H, J=8.2 Hz, amide), δ 7.69 ppm (d, 1H, J=8.2 Hz, phthalic), δ 7.91 ppm (d, 1H, J=8.2 Hz, phthalic), δ 8.11 ppm (s, 1H, phthalic).

5-Fluoresceinamine was brominated to generate 5-eosinamine, which was converted into 5-mercaptoeosin in analogous way to the 5-mercaptofluorescein. In a nucleo-

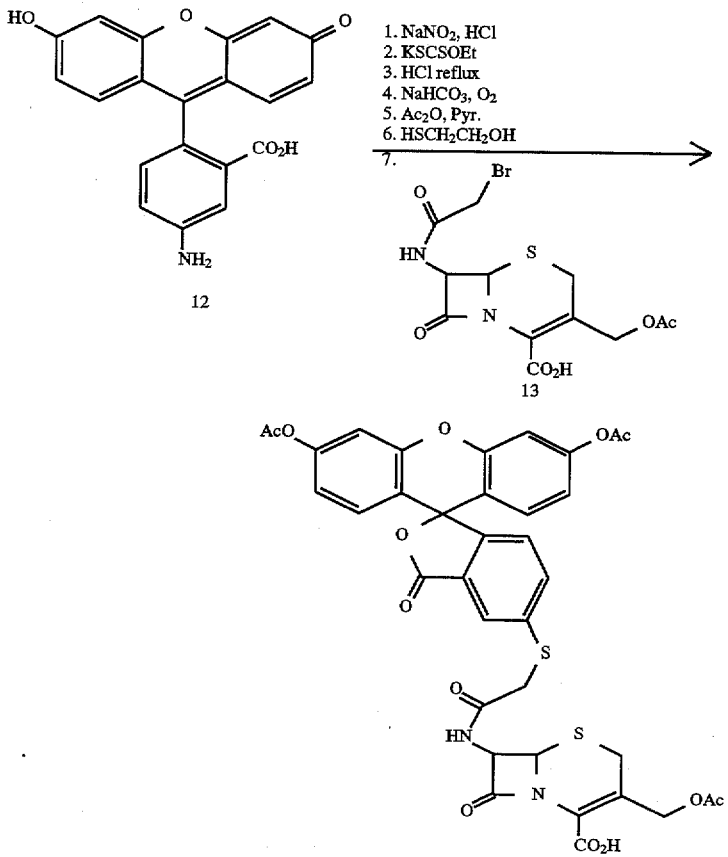

philic displacement of the cephalosporin acetate by 5-mercaptoeosin diacetate the FRET-cephalosporin was generated as the protected tetraacetyl derivative.

dropwise over the period of one hour. After another 2 hours at 0° C. 20 g of ice was slowly added. The flask was put on the high vacuum pump in the cold, to remove excess nitrous

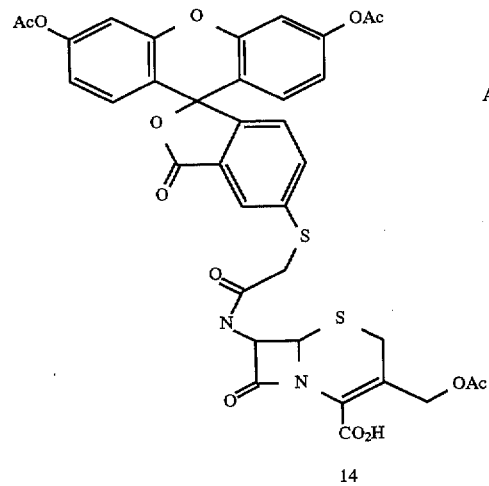

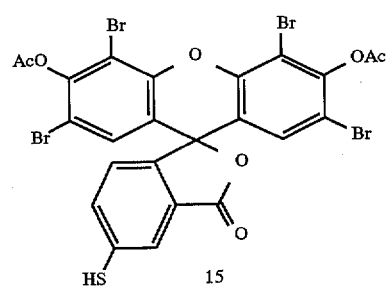

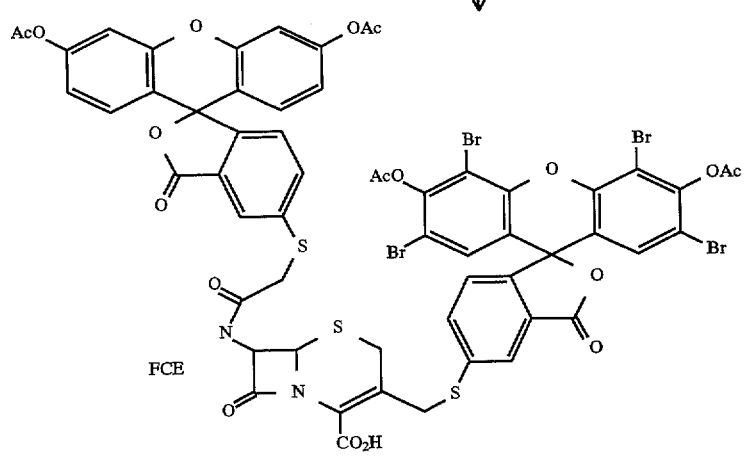

To prepare 5-eosinamine, 1.74 g (5 mmol) 5-fluoresceinamine was suspended in 30 ml glacial acetic and 2.06 ml (40 mmol, 1(100% excess) bromine was added. With the addition of bromine the fluoresceinamine went into solution. The solution was heated for six hours at 90° C., during which period a white precipitate began to form. An ice-cooled trap attached to the flask kept bromine from escaping into the atmosphere. Excess bromine was then recovered by distillation into a liquid nitrogen cooled collecting flask. One volume of water was added to the acetic acid solution to precipitate any product remaining in solution. The precipitate was collected by filtration and dissolved in 1N aqueous sodium hydroxide. 5-Eosinamine was precipitated as the free amine by addition of glacial acetic acid. The eosinamine was dissolved in little chloroform and methanol was added. Concentrating this solution on the rotary evaporator gave 2.56 g (3.85 mmol, 77%) eosinamine as a fine white powder (the eosinamine-spirolactone).

To prepare 5-eosin-ethylxanthate diacetate, 670 mg (1 mmol) 5-eosinamine were stirred in 2 ml concentrated sulfuric acid and 2 ml glacial acetic acid. The suspension was cooled with an ice-salt bath to a few degrees below 0° C., which turned it into a thick paste that was difficult to stir. 200 mg (2.9 mmol) sodium nitrite in 1 ml water were added gases (caution!!). Saturated ice-cold aqueous sodium bicarbonate solution was added until the solids dissolved into the dark red solution. 200 mg (1.2 mmol) Potassium ethylxanthate was added and a pink precipitate formed (5-eosindiazonium xanthate). A few crystals of nickel(II) chloride catalyzed the conversion of the diazonium salt with evolution of nitrogen. Once nitrogen evolution had ceased the products were precipitated with 1N hydrochloric acid. The precipitate was collected by filtration and dried in vacuo. It was treated with acetic anhydride-pyridine (1:1) at 40° C. for one hour. After removal of the reagents in vacuo, the residue was chromatographed over silica gel with ethyl acetate-hexane (1:4) as eluent. The desired product eluted first. The yield was 110 mg (0.13 mmol, 13%) of the title compound as a white powder.

For preparation of the disulfide direct of 5-eosinthiol diacetate (dimer of 15), 110 mg (0.13 mmol) 5-eosin-ethylxanthate diacetate was stirred in 10 ml concentrated (30%) aqueous ammonia and the solution was heated to 70° C. Air was bubbled slowly through the solution to oxidize the thiol to the disulfide in situ. After 2 hours the solvents were removed on the rotary evaporator at 40° C. and the residue was treated with acetic anhydride-pyridine (1:1). After removal of the reagents in vacuo the residue was chromatographed over silica gel with ethyl acetate-hexane (1:4) as the eluent. Yield was 90 mg (60 µmol, 91%) of the title product as a white powder. The compound was reduced to the monomer (15) by dissolving it in methanol with addition of sodium acetate and addition of 20 equivalents mercaptoethanol. After 2 hours the methanolic solution was poured into 3 volumes 5% aqueous acetic acid from which the precipitating 5-fluoresceinthiol monomer was collected by centrifugation. The solid was washed with water until no odor of mercaptoethanol remained.

Coupling of diacetyl 5-eosinthiol (15) with 7β-[(5-diacetylfluorescein)thio]acetamido-3-(acetoxymethyl)-3-cephem-4-carboxylic acid (14) and deacylation with acetylesterase was effected as follows. 10 mg (13 µmol) 7β-[(5-Diacetylfluorescein)thio]acetamido-3-(acetoxymethyl)-3-cephem-4-carboxylic acid and 10 mg (13 µmol) diacetyl-5-eosinthiol were dissolved in 200 µl dry acetonitrile and the solution was sealed under argon in a glass tube. The tube was kept in an oil bath at 84° C. (±2° C.) for 16 hours. Then it was cut open, the solution transferred to a flask and the solvent removed in vacuo. The residue was flash-chromatogaphed over silica gel with ethyl acetate-methanol-acetic acid (100:1:1) as the eluent. Deprotection of the acetates was achieved by incubating fine product with orange peel acetylesterase in 50 mM phosphate buffer (pH7) for 24 hours at 37° C. The deacylated product was purified by $C_{18}$ reverse phase chromatography. The eluent was a step gradient of 25 mM aqueous phosphate buffer (pH7) and methanol. Fluorescein byproducts eluted with 33% and 50% methanol in the eluent, after which the desired product eluted in 66% methanol.

The deprotected compound shows little fluorescence in phosphate buffer as the two hydrophobic dyes stack. The remaining fluorescence is due to fluorescence resonance energy transfer (FRET). This compound is a good substrate for RTEM β-lactamase and will be referred to as FCE.

Figure 2:
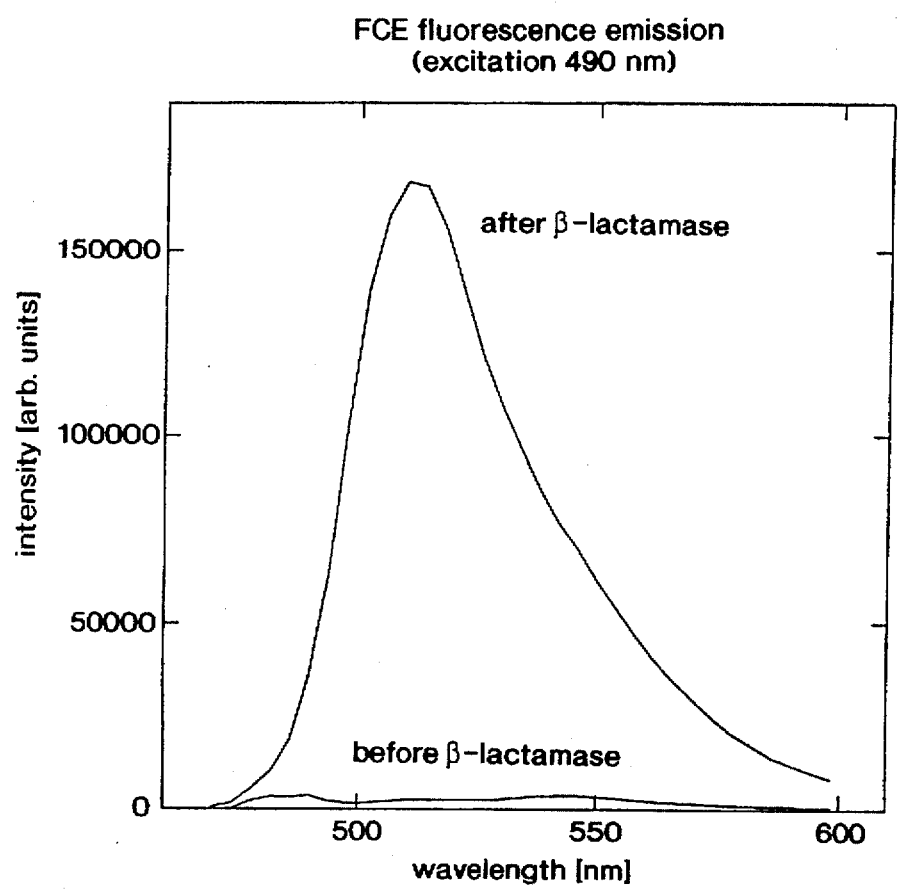
FIG. 2 illustrates the emission spectrum of compound 17 before and after β-lactamase cleavage of the β-lactam ring.

Cleavage of the compound increases fluorescence at 515 nm about 70-fold (FIG. 2). The fluorescence properties of the compound can be attributed to dye-dimer formation, as FRET increases drastically once methanol is added to the solution. Methanol breaks the hydrophobic interaction that causes the fluorophores to stack.

Example 3 (compound 22)

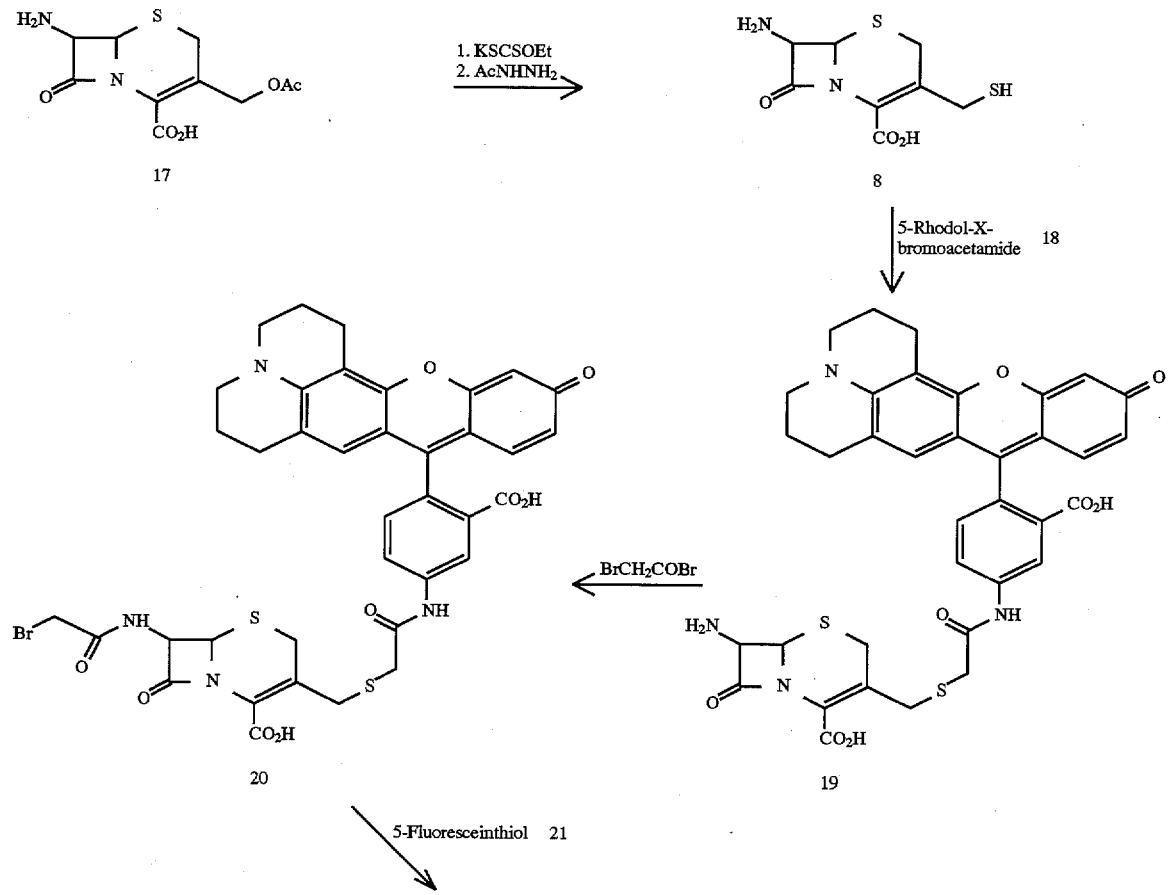

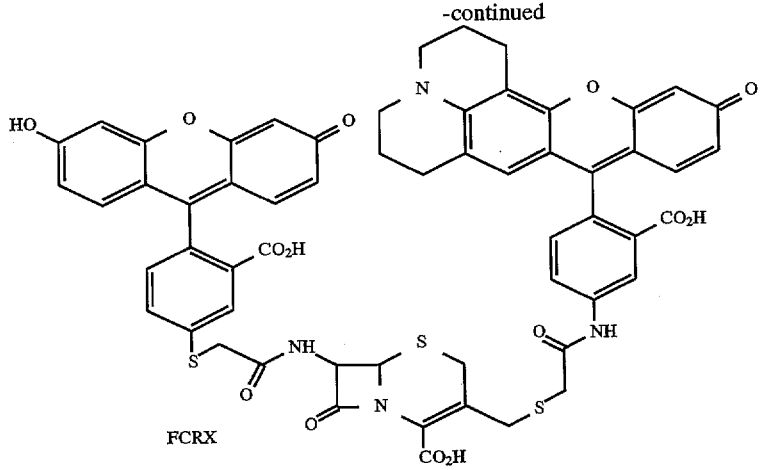

FCRX

The 3'-acetate of 7-aminocephalosporanic acid was displaced by ethylxanthate [Van Heyningen and Brown (1965), supra] which was hydrolysed to the free sulfhydryl with aqueous acetylhydrazine [Japanese Patent, Kokai 75/18494, CA85, 97320d]. The sulfhydryl group was reacted with 5-bromoacetamido-rhodol-X in aqueous dimethylformamide. The cephalosporin 7-amine was reacted with bromoacetyl bromide in aqueous dioxane, followed by bromide displacement with 5-fluoresceinthiol to yield a FRET-cephalosporin that is virtually nonfluorescent in 50 mM phosphate buffer pH 7. This compound is referred to as FCRX.

The first step in preparation of 5-rhodol-X-bromoacetamide was synthesis of 9-(2'-carboxy-4'(5')-nitro-benzoyl)-8-hydroxyjulolidine and separation of the isomers. 10.1 g (48 mmol, 92% purity) 4-Nitrophthalic anhydride were dissolved in 20 ml toluene at 70° C. 9.76 g (50 mmol, 97% purity) 8-Hydroxyjulolidine in 20 ml ethyl acetate were added and the solution kept at 70° C. for 30 min. The reaction mixture was run through a short bed of silica gel followed by ethyl acetate as eluent. The solvents were removed in vacuo and the solid redissolved in a minimum amount of refluxing ethyl acetate. The isomer with the nitro-group meta to the benzoic acid crystallizes over night from solution in orange crystals (3.47 g in first fraction). After additional fractional crystallization the pure isomer was obtained. $^1$H NMR (CDCl$_3$) of crystallized isomer: δ 1.91 ppm (m, 4H, aliphatic methylenes), δ 2.73 ppm, 2.46 ppm (2 m, 4H, aniline methylenes), δ 3.26 ppm (m, 4H, benzylic methylenes), δ 6.32 ppm (s, 1H, julolidine), δ 7.53 ppm (d, 1H, J=8.4 Hz, phthalic), δ 8.43 ppm (dd, J$_1$=8.4 Hz, J$_2$=2.2 Hz, phthalic), δ 8.90 ppm (d, 1H, J=2.2 Hz, phthalic).

For preparation of 5-rhodol-X-amine hydrochloride (named by analogy with rhodamine-X), 1.91 g (5.0 mmol) 9-(2'-Carboxy-4'-nitro-benzoyl)-8-hydroxyjulolidine was stirred in 5 ml concentrated (96%) sulfuric acid. 700 mg (6.4 mmol, 1.25 equ.) resorcinol was added with cooling over a period of 15 minutes. The suspension was stirred 1.5 hours at room temperature and then poured into 200 ml water with vigorous stirring. The purple precipitate was collected by filtration and redissolved in 75 ml water with the help of 5.3 g (22 mmol) sodium sulfide nonahydrate. 2.5 g (44.6 mmol) Anhydrous sodium bisulfide was added and the solution refluxed for 24 hours. Then, after cooling to room temperature, the product was precipitated by addition of glacial acetic acid. The solid was collected by filtration and boiled with 100 ml half-saturated aqueous hydrochloric acid. The solution was filtered hot through a glass frit to remove sulfur. The solution volume was reduced to 10 ml on the rotary evaporator. 1 Volume saturated brine was added and the precipitate collected by filtration. Crystallization from refluxing hydrochloric acid yielded 1.78 g (3.85 mmol, 77%) dark red crystals 5-rhodol-X-amine hydrochloride. $^1$H NMR (dDMSO) of 5-nitro-rhodol-X: δ 1.90 ppm, 2.05 ppm (2m, 4H, aliphatic methylenes), δ 2.72 ppm, 3.03 ppm (2 m, 4H, anilinic methylenes), δ 3.66 ppm (m, 4H, benzylic methylenes), δ 6.90 ppm (s, 1H, xanthene), δ 6.96 ppm (dd, 1H, J$_1$=9.0 Hz, J$_2$=2.1 Hz, xanthene), δ 7.11 ppm (d, 1H, J=9.0 Hz, xanthene), δ 7.22 ppm (d, 1H, J=2.1 Hz, xanthene), δ 7.78 ppm (d, 1H, J=8.4 Hz, phthalic), δ 8.70 ppm (dd, 1H, J$_1$=8.4 Hz, J$_2$=2.4 Hz, phthalic), δ 8.91 ppm (d, 1H, J=2.4 Hz, phthalic). $^1$H NMR (CD$_3$OD) of 5-rhodol-X-amine hydrochloride: δ 2.00 ppm, 2.14 ppm (2 m, 4H, aliphatic methylenes), δ 2.75 ppm, 3.11 ppm (2 m, 4H, anilinic methylenes), δ 3.67 ppm (m, 4H, benzylic methylenes), δ 6.85 ppm (s, 1H, xanthene), δ 6.94 ppm (dd, 1H, J$_1$=9.0 Hz, J$_2$=2.1 Hz, xanthene), δ 7.13 ppm (d, 1H, J=9.0 Hz, xanthene), δ 7.16 ppm (d, 1H, J=2.1 Hz, xanthene), δ 7.551 ppm (d, 1H, J=8.1 Hz, phthalic), δ 7.82 ppm (dd, 1H, J$_1$=8.1 Hz, J$_2$=1.9 Hz, phthalic), δ 8.28 ppm (d, 1H, J=1.9 Hz, phthalic).

Preparation of 5-rhodol-X-bromoacetamide (18) was effected as follows. 115 mg (0.25 mmol) 5-Rhodol-X-amine hydrochloride were dissolved with 180 mg (2.1 mmol) sodium bicarbonate in 2 ml water-dioxane (1:1). The solution was cooled on ice and 175 μl, (2 mmol) bromoacetyl-bromide were added with stirring over a period of 20 minutes. The solution was then kept at room temperature for 1.5 hours, after which 5 volumes of water were added. The dioxane was removed on the rotary evaporator, and the product was precipitated from the remaining aqueous solution by addition of acetic acid. The precipitate was filtered off and dissolved in a small volume of chloroform-methanol (1:1). Silica gel was added to the solution and the solvents removed in vacuo. The solids were applied to a silica gel column and the product eluted with methanol-ethyl acetate (1:4). This eluent did dissolve some silica gel which remained with the eluted product. $^1$H NMR (CD$_3$OD, 10% dDMSO): δ 1.98 ppm, 2.12 ppm (2 m, 4H, aliphatic methylenes), δ 2.72 ppm, 3.06 ppm (2 m, 4H, anilinic methylenes), δ 3.56 ppm (m, 4H, benzylic methylenes), δ

4.08 ppm (s, 2H, bromoacetyl), δ 6.79 ppm (dd, 1H, $J_1$=9.2 Hz, $J_2$=2.1 Hz, xanthrene), δ 6.83 ppm (s, 1H, xanthene), δ 6.90 ppm (d, 1H, J=2.1 Hz, xanthene), δ 7.19 ppm (d, 1H, J=9.2 Hz, xanthene), δ 7.24 ppm (d, 1H, J=8.4 Hz, phthalic), δ 8.02 ppm (dd, 1H, $J_1$=8.4 Hz, $J_2$≈1 Hz, phthalic), δ 8.30 ppm (d, 1H, J≈1 Hz, phthalic).

For preparation of 7β-(bromoacetamido)-3-[[[(5-rhodol-X-amido)methyl]thio]methyl]-3-cephem-4-carboxylic acid (20), 4.5 mg (10 μmol) 5-Rhodol-X-bromoacetamide (18) were dissolved in 0.5 ml 250 ml phosphate buffer adjusted to pH 7.7 and 0.5 ml dimethylformamide. The solution was deoxygenated and 10 mg (40 μmol) 7β-amino-3-(thiomethyl)-3-cephem-4-carboxylic acid (8) prepared according to the literature procedure in 100 μl phosphate buffer was added in an argon atmosphere. The solution was kept for 2 hours at 30° C. Then the solvents were removed in vacuo and the residue dissolved in 1 ml water, from which the product was precipitated by addition of acetic acid. The precipitate was collected and the product purified by $C_{18}$ reverse-phase chromatography with 0.1% trifluoroacetic acid in 35% methanol/water as eluent.

The above product (19) was dissolved 1 ml dioxane-water (1:1) with 20 mg sodium bicarbonate. 10 μl Bromoacctyl bromide were added to the solution on ice. The solution was kept for another 1.5 hours at room temperature. 20 mg sodium bicarbonate and 10 μl bromoacetyl bromide were added to the solution with ice cooling. After another 1.5 hours at room temperature the dioxane was removed on the rotary evaporator and the products were precipitated from the aqueous solution with 1M phosphoric acid and collected by centrifugation. The solids were suspended in dilute aqueous bicarbonate solution and the undissolved particles removed by centrifugation and discarded. The product was precipitated with 1M phosphoric acid and purified by flash chromatography on silica gel with chloroform-methanol-acetic acid-water (55:15:4:2). This procedure dissolved small amounts of silica gel.

Coupling of diacetyl 5-fluoresceinthiol (21) with 7β-(bromoacetamido)-3-[[[(5-rhodol-X-amido)methyl]thio]methyl]-3-cephem-4-carboxylic acid (20) was effected as follows. 7β-(Bromoacetamido)-3-[[[(5-rhodol-X-amido)methyl]thio]methyl]-3-cephem-4-carboxylic acid was reacted with a 50% excess of 5-fluoresceinthiol under argon with dimethylformamide-(250 mM aqueous phosphate buffer pH 7.7) (1:1) as the solvent. The product was purified from excess fluoresceinthiol by repeated dissolution in methanol and precipitation in ethyl acetate.

Figure 3:
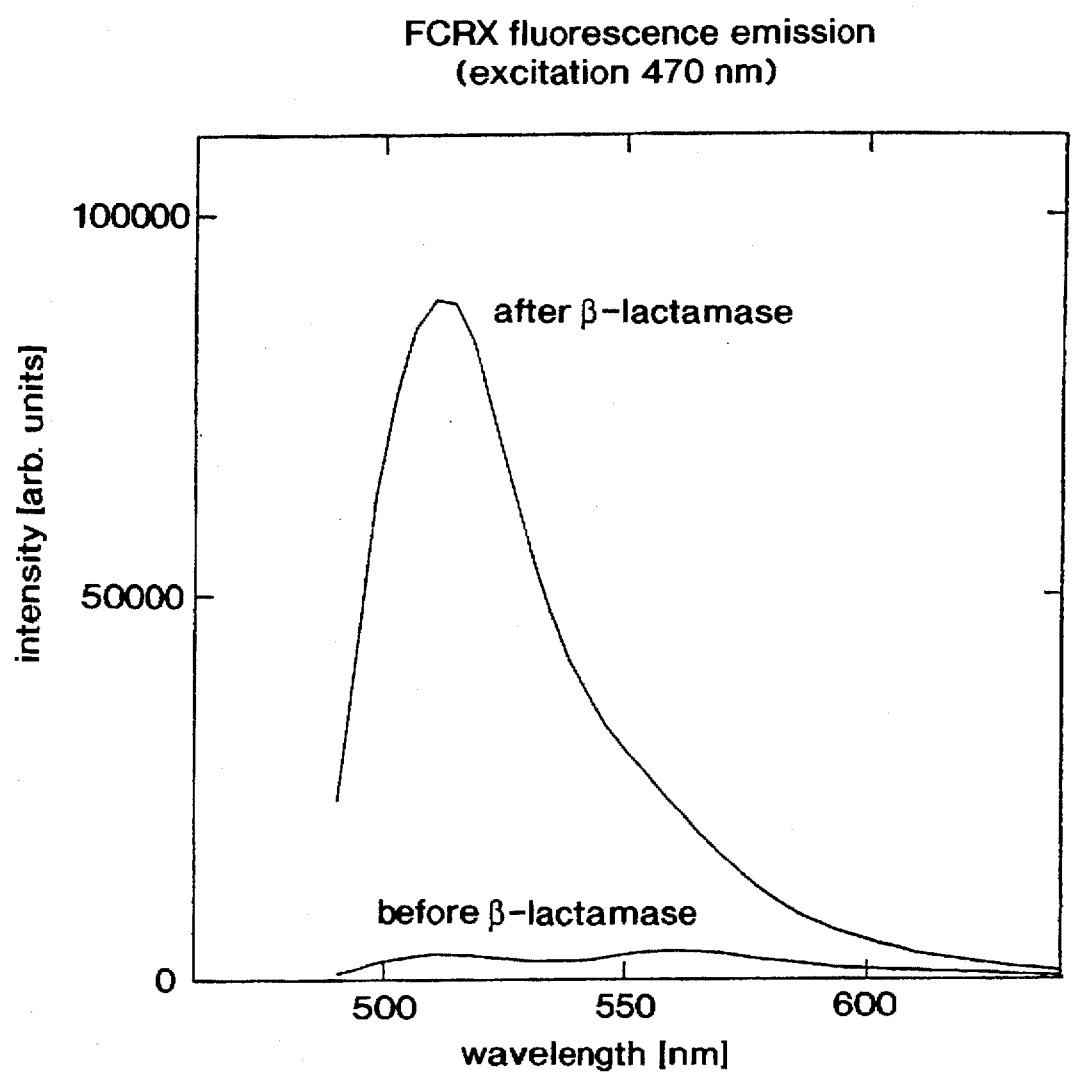
FIG. 3 illustrates the emission spectrum of compound 22 before and after β-lactamase cleavage of the β-lactam ring.

FIG. 3 shows the fluorescence emission spectra of this FRET-cephalosporin in 50 mM phosphate buffer pH 7 before and after treatment with β-lactamase. The low initial fluorescence is due to the stacking of the fluorophores, forming a ground state complex that is nonfluorescent. When one adds methanol to the solution this stacking can be disrupted and efficient fluorescence resonance energy transfer occurs.

Example 4 (compound 25)

N-[resorufin-4-carbonyl]-N'-iodoacetyl-piperazine (Boehringer Mannheim) was attached to the cephalosporin as a FRET-acceptor for fluorescein. It is referred to as FCRE.

The FRET-cephalosporin FCRE (25) carrying fluorescein as the donor and resorufin as the quencher was made by the same procedure as the one carrying the rhodol-X-acceptor. The N-[resorufin-4-carbonyl]-N'-iodoacetyl-piperazine (Boehringer Mannheim) was coupled to the free 3'-thiol of the cephalosporin followed by bromoacetylation and addition of the 5-fluoresceinthiol. In departure from the protocol, three equivalents of 5-fluorescein thiol were added, as the first equivalent instantaneously reduced the resorufin and formed unreactive difluorescein-disulfide. Exposure to air reoxidized resorufin to the original dye.

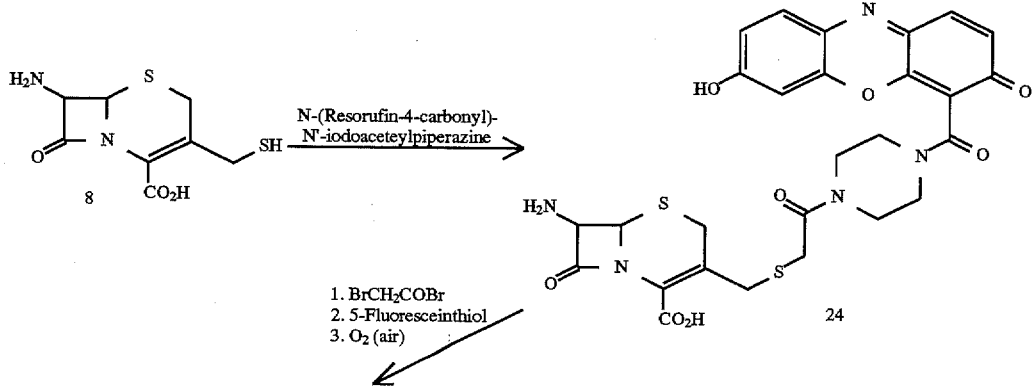

Figure 4:
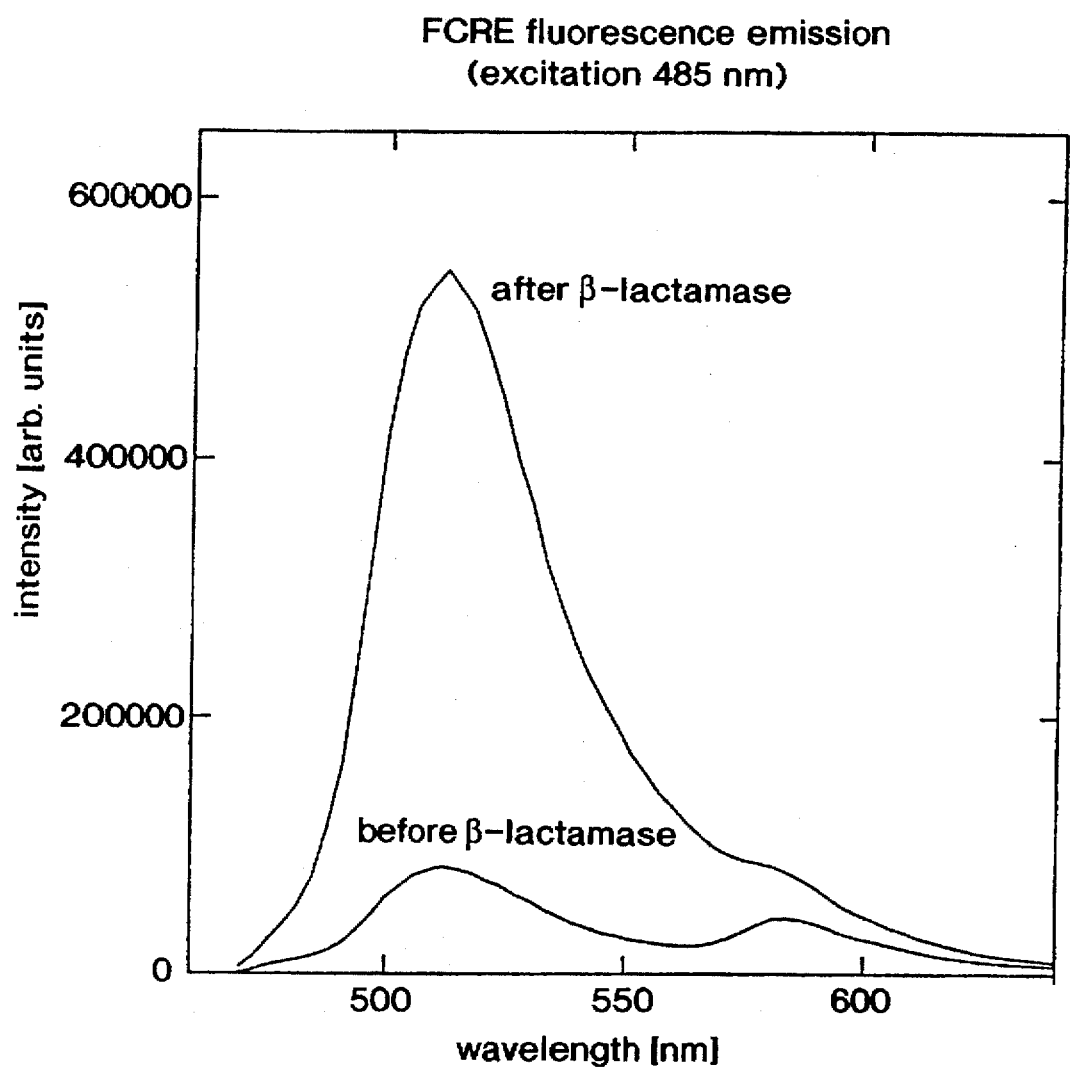
FIG. 4 illustrates the emission spectrum of compound 25 before and after β-lactamase cleavage of the β-lactam ring.

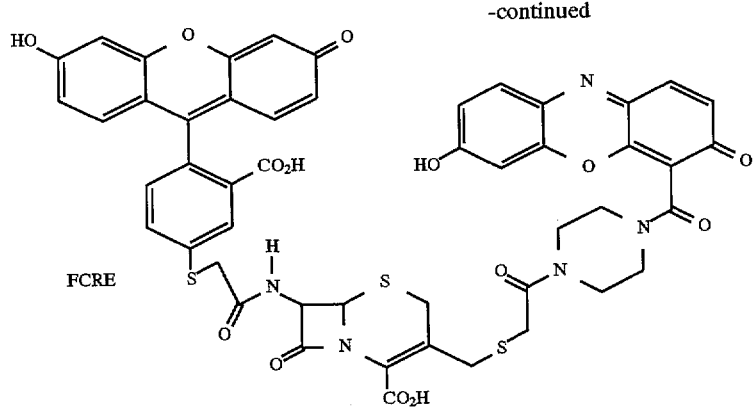

β-Lactamase catalyzed hydrolysis of this compound generates two fluorescent fragments. Resorufin excitation and emission spectra are longer wavelength and narrower than the rhodol spectra, possibly affording better spectral separation between the uncleaved dye versus the products of enzymatic cleavage. But, as in the case of rhodol as the acceptor, in aqueous phosphate buffer the dyes stack and form a dark complex. β-Lactamase treatment disrupts the stacking and increases donor fluorescence (FIG. 4).

Example 5 (compound 7b)

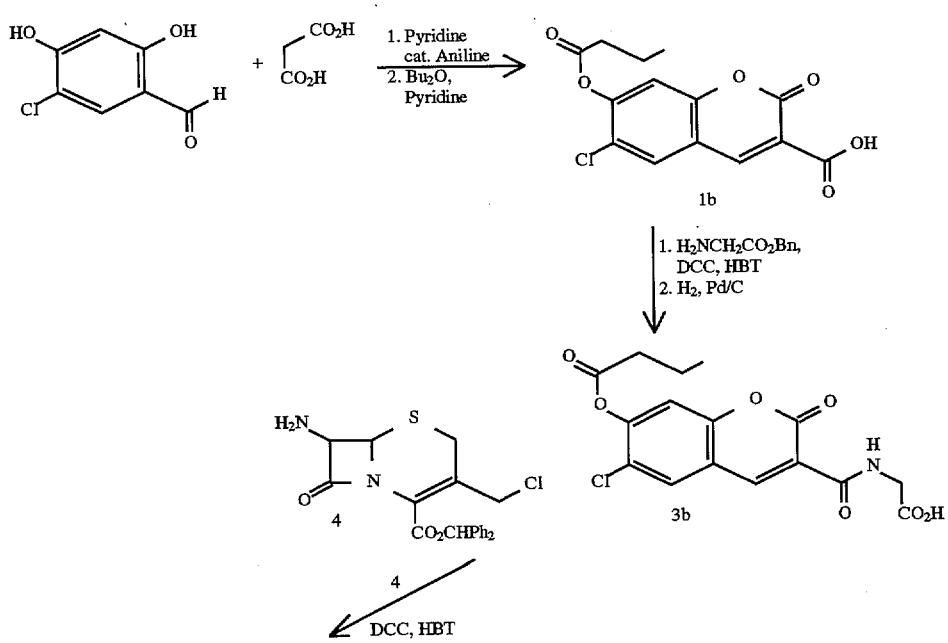

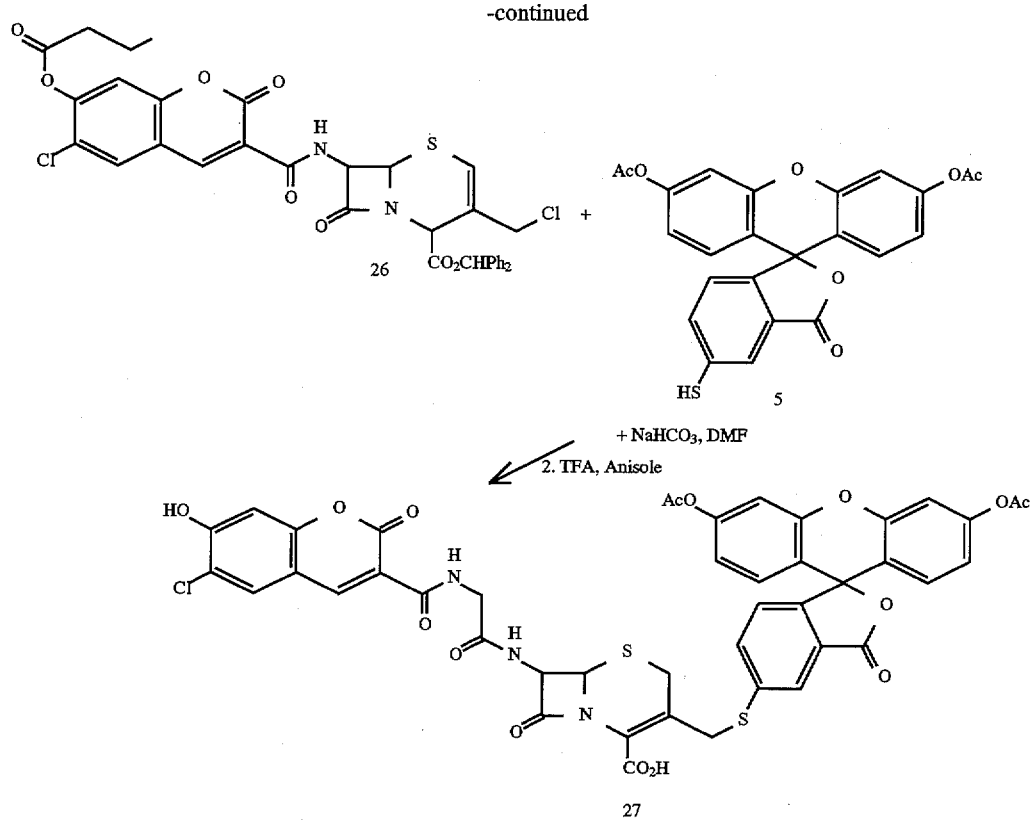

For synthesis of 2,4 dihydroxy-5-chlorobenzaldehyde, 21.7 g (0.15 Mol) 4-chlororesorcinol were dissolved in 150 ml dry diethyl ether and 27 g finely powdered zinc (II) cyanide and 0.5 g potassium chloride were added with stirring. The suspension was cooled on ice. A strong stream of hydrogen chloride gas was blown into the solution with vigorous stirring. After approximately 30 minutes the reactants were dissolved. The addition of hydrogen chloride gas was continued until it stopped being absorbed in the ether solution (approx. 1 hour). During this time a precipitate formed. The suspension was stirred for one additional hour on ice. Then the solid was let to settle. The ethereal solution was poured from the solid. The solid was treated with 100 g of ice and heated to 100° C. in a water bath. Upon cooling the product crystallized in shiny plates from the solution. They were removed by filtration on dried over potassium hydroxide. The yield was 15.9 g (0.092 Mol, 61%). $^1$H NMR (CDCl$_3$): δ 6.23 ppm (s, 1H, phenol), δ 6.62 ppm (s, 1H, phenyl), δ 7.52 ppm (s, 1H, phenyl), δ 9.69 ppm (s, 1H, formyl), δ 11.25 ppm (s, 1H, phenol).

To prepare 3-carboxy 6-chloro 7-hydroxy coumarin, 5.76 g (0.033 Mol) 2,4-dihydroxy-5-chlorobenzaldehyde and 7.2 g (0.069 Mol) malonic acid were dissolved in 5 ml warm pyridine. 75 μl Aniline were stirred into the solution and the reaction let to stand at room temperature for 3 days. The yellow solid that formed was broken into smaller pieces and 50 ml ethanol was added. The creamy suspension was filtered through a glass frit and the solid was washed three times with 1N hydrochloric acid and then with water. Then the solid was stirred with 100 ml ethyl acetate, 150 ml ethanol and 10 ml half concentrated hydrochloric acid. The solvent volume was reduced in vacuo and the precipitate recovered by filtration, washed with diethyl ether and dried over phosphorous pentoxide. 4.97 g (0.021 Mol, 63%) of product was obtained as a white powder. $^1$H NMR (dDMSO): δ 6.95 ppm (s, 1H), δ 8.02 ppm (s, 1H), δ 8.67 ppm (s, 1H).

To prepare 7-butyryloxy 3-carboxy 6-chloro coumarin, 3.1 g (12.9 mMol) 3-carboxy 6-chloro 7-hydroxy coumarin were dissolved in 100 ml dioxane and treated with 5 ml butric anhydride, 8 ml pyridine and 20 mg dimethyl aminopyrictine at room temperature for two hours. The reaction solution was added with stirring to 300 ml heptane upon which a white precipitate formed. It was recovered by filtration and dissolved in 150 ml ethyl acetate. Undissolved material was removed by filtration and the filtrate extracted twice with 50 ml 1N hydrochloric acid/brine (1:1) and then brine. The solution was dried over anhydrous sodium sulfate. Evaporation in vacuo yielded 2.63 g (8.47 mMol, 66%) of product. $^1$H NMR (CDCl$_3$): δ 1.08 ppm (t, 3H, J=7.4 Hz, burtric methyl), δ 1.85 ppm (m, 2H, J$_1$≈J$_2$=7.4 Hz, butyric methylene), δ 2.68 ppm (t, 2H, J=7.4 Hz, butyric methylene), δ 7.37 ppm (s, 1H, coumarin), δ 7.84 ppm (s, 1H, coumarin), δ 8.86 ppm (s, 1H, coumarin).

Preparation of 7-butyryloxy-3-carbonyl-O-benzyl-gylcine-6-chloro-coumarin is effected as follows. 2.5 g (8.06 mMol) 7-Butyryloxy-3-carboxy 6-chloro coumarin, 2.38 g hydroxybenztriazole hydrate (16 mMol) and 1.67 g (8.1 mMol) dicyclohexyl carbodiimide were dissolved in 30 ml dioxane. A toluene solution of O-benzylglycine [prepared by extraction of 3.4 a (10 mMol) benzylglycine tosyl salt with ethyl acetate-toluene-saturated aqueous bicarbonate-water (1:1:1:1, 250 ml), drying of the organic phase with anhydrous sodium sulfate and reduction of the solvent volume to 5 ml] was added dropwise to the coumarin solution. The reaction was kept at room temperature for 20 hours after which the precipitate was removed by filtration and washed extensively with ethylacetate and acetone. The combined solvent fractions were reduced to 50 ml on the rotatory evaporator upon which one volume of toluene was added and the volume further reduced to 30 ml. The precipitating product was recovered by filtration and dissolved in 200 ml chloroform-absolute ethanol (1:1). The solution was reduced to 50 ml on the rotatory evaporator and the product filtered off and dried in vacuo yielding 1.29 g of the title product. Further reduction of the solvent volume yielded a second crop (0.64 g). Total yield: 1.93 g (4.22 mMol, 52%). $^1$H NMR (CDCl$_3$): δ 1.08 ppm (t, 3H, J=7.4 Hz, butyric methyl), δ 1.84 ppm (m, 2H, J$_1$≈J$_2$=7.4 Hz, butyric methylene), δ 2.66 ppm (t, 2H, J=7.4 Hz, butyric methylene), δ 4.29 ppm (d, 2H, J=5.5 Hz, glycine methylene), δ 5.24 ppm (s, 2H, benzyl), δ 7.36 ppm (s, 1H, coumarin), δ 7.38 ppm (s, 5H, phenyl), δ 7.77 ppm (s, 1H, coumarin), δ 8.83 ppm (s, 1H, coumarin), δ 9.15 ppm (t, 1H, J=5.5 Hz, amide).

7-Butyryloxy 3-carbonylglycine 6-chlorocoumarin was prepared as follows. 920 mg (2 mMol) 7-Bulyryloxy 3-carbonyl-O-benzyl-glycine 6-chlorocoumarin were dissolved in 50 ml dioxane. 100 mg palladium on carbon (10%) and 100 μl acetic acid were added to the solution and the suspension stirred vigorously in a hydrogen atmosphere at ambient pressure. After the uptake of hydrogen seized the suspension was filtered. The product containing carbon was extracted five times with 25 ml boiling dioxane. The combined dioxane solutions were let to cool upon which the product precipitated as a white powder. Reduction of the solvent to 20 ml precipitates more product. The remaining dioxane solution is heated to boiling and heptane is added until the solution becomes cloudy. The weights of the dried powders were 245 mg, 389 mg and 58 mg, totaling 692 mg (1.88 mMol, 94%) of white product. $^1$H NMR (dDMSO): δ 1.02 ppm (t, 3H, J=7.4 Hz, butyric methyl), δ 1.73 ppm (m, 2H, J$_1$≈J$_2$=7.3 Hz, butyric methylene), δ 2.70 ppm (t, 2H, J=7.2 Hz, butyric methylene), δ 4.07 ppm (d, 2H, J=5.6 Hz, glycine methylene), δ 7.67 ppm (s, 1H, coumarin), δ 8.35 ppm (s, 1H, coumarin), δ 8.90 ppm (s, 1H, coumarin), δ 9.00 ppm (t, 1H, J=5.6 Hz, amide).

Coupling of 7-butyryloxy-3-carbonylglycine 6-chlorocoumarin with 7-amino-3'-chloro cephalosporanic acid benzhydryl ester was effected as follows. 368 mg (1 mMol) 7-Butyryloxy-3-carbonylglycine-6-chlorocoumarin, 270 mg hydroxybenztriazole hydrate and 415 mg (1 mMol) 7-amino-3'-chloro cephalosporanic acid benzhydryl ester were suspended in 40 ml dioxane-acetonitrile (1:1). 260 mg (1.25 mMol) dicyclohexyl carbodiimide in 5 ml acetonitrile were added and the suspension was stirred vigorously for 36 hours. The precipitate was removed by filtration and the volume of the solution reduced to 20 ml on the rotatory evaporator. 50 ml Toluene was added and the volume reduced to 30 ml. With stirring 50 ml heptane was added and the suspension chilled on ice. The precipitate was recovered by filtration. It was redissolved in 10 ml chloroform and the remaining undissolved solids were filtered off. Addition of 2 volumes of heptane precipitated the title product which was collected and dried in vacuo and yielded 468 mg (0.64 mMol, 64%) off-white powder. $^1$H NMR (CDCl$_3$): δ 1.08 ppm (t, 3H, J=7.4 Hz, butyric methyl), δ 1.84 ppm (m, 2H, J$_1$≈J$_2$=7.4 Hz, butyric methylene), δ 2.66 ppm (t, 2H, J=7.4 Hz, butyric methylene), δ 3.54 ppm (2d, 2H, J=18.3 Hz, cephalosporin C-2), δ 4.24 ppm (2d, 2H, J=5.8 Hz, cephalosporin 3 methylene), δ 4.37 ppm (d, 2H, J=3.8 Hz, glycine methylene), δ 5.02 ppm (d, 1H, J=4.9 Hz, cephalosporin C-6), δ 5.89 ppm (dd, 1H, J$_1$=9.0 Hz, J$_2$=5.0 Hz, cephalosporin C-7), δ 6.96 ppm (s, 1H, benzhydryl), δ 7.30–7.45 ppm (m, 12H, phenyl, coumarin, amide), δ 7.79 ppm (s, 1H, coumarin), δ 8.84 ppm (s, 1H, coumarin), δ 9.28 ppm (t, 1H, J=3.7 Hz, amide).

Coupling of the above product with 5-fluoresceinthiol was effected as allows. 90 mg (0.2 mMol) 5-mercaptofluorescein diacetate disulfide dimer were dissolved in 10 ml chlorolform treated with 25 μl tributyl phosphine and 25 μl water in an argon atmosphere. The solution was kept for 2 hours at ambient temperature and was then added to a solution of 20 mg sodium bicarbonate, 25 mg sodium iodide and 110 mg (0.15 mMol) of the above compound in 10 ml dimethylformamide. After 4 hours the solvents were removed in vacuo and the residue triturated with diethylether. The solid was dissolved in ethyl acetate-acetonitrile (1:1). After removal of the solvents the residue was triturated once more with diethylether yielding 157 mg (0.13 mMol, 88%) of a cream colored powder product.

A sample of the above compound was treated with a large access of trifluoroacetic acid-anisole (1:1) at room temperature for 20 minutes. The reagents are removed in vacuo and the residue triturated with ether. High performance liquid chromatography of the solid in 45% aqueous acetonitrile containing 0.5% acetic acid gives a product in which the butyrate and the diphenylmethyl esters have been cleaved. It was purified by high performance liquid chromatography on a reverse phase C$_{18}$-column using 45% aqueous acetonitrile containing 5% acetic acid as line eluent.

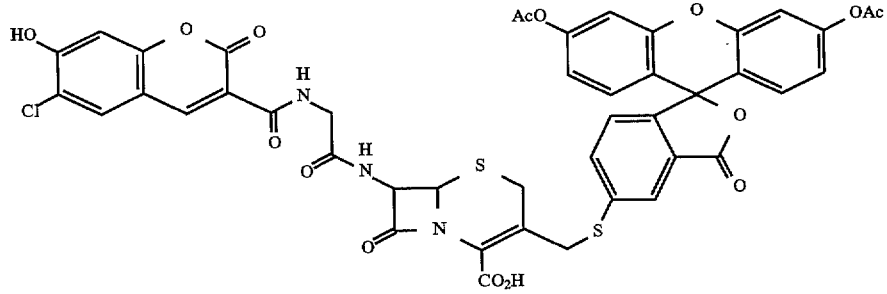

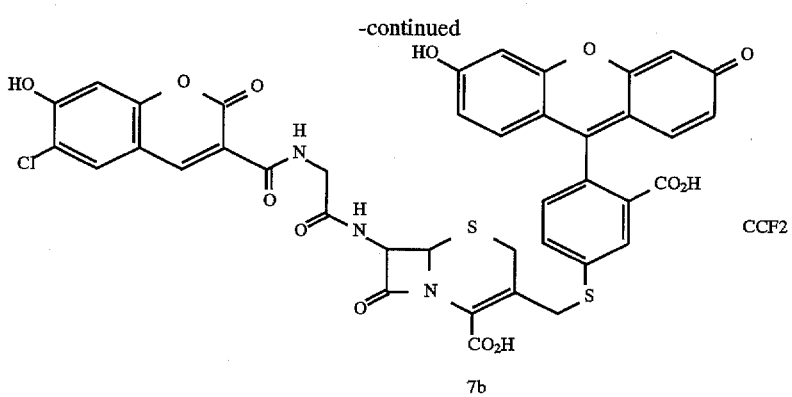

CCF2

7b

Deprotection of the fluorescein acetates in compound 27 was accomplished with sodium bicarbonate in methanol (room temperature, 30 minutes) to provide the fluorescent enzyme substrate CCF2. It was purified by high performance liquid chromatography on a reverse phase $C_{18}$-column using 35% aqueous acetonitrile containing 0.5% acetic acid as the eluent.

ing 0.5% acetic acid as the eluent. CCF2/$ac_2AM_2$ is readily converted to CCF2 in the cells' cytoplasm.

Unlike in Examples 1–4, the donor and acceptor dyes in substrate CCF2 do not stack. The substrate is fully fluorescent in phosphate buffer and there is no formation of the "dark complex" (i.e., addition of methanol does not change the fluorescence spectrum of CCF2, except for the effect of

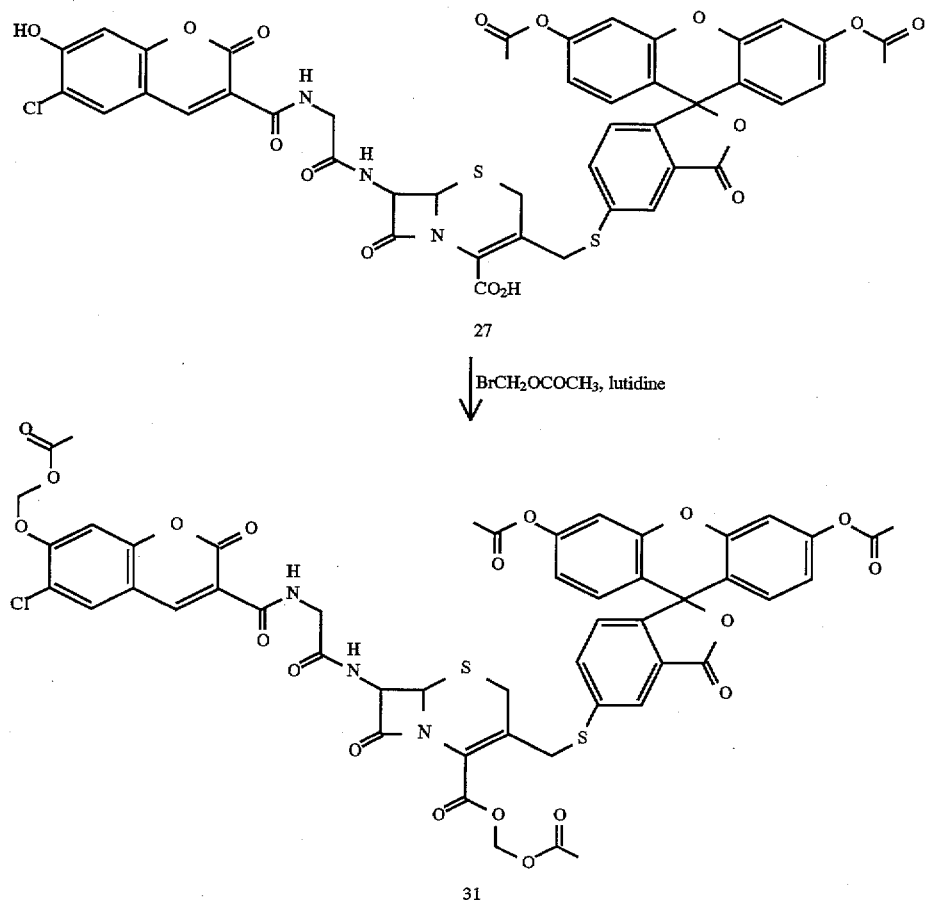

Stirring of compound 27 with excess acetoxymethylbromide in dry lutidine produced the membrane permeable derivative of the substrate (CCF2/$ac_2AM_2$). It was purified by high performance liquid chromatography on a reverse phase $C_{18}$-column using 65% aqueous acetonitrile containdilution). This is due to the much smaller and more polar nature of the 7-hydroxycoumarin compared to that of the xanthene dyes (eosin, rhodamine, rhodol and resorufin) in Examples 1–4.

43

Figure 5:
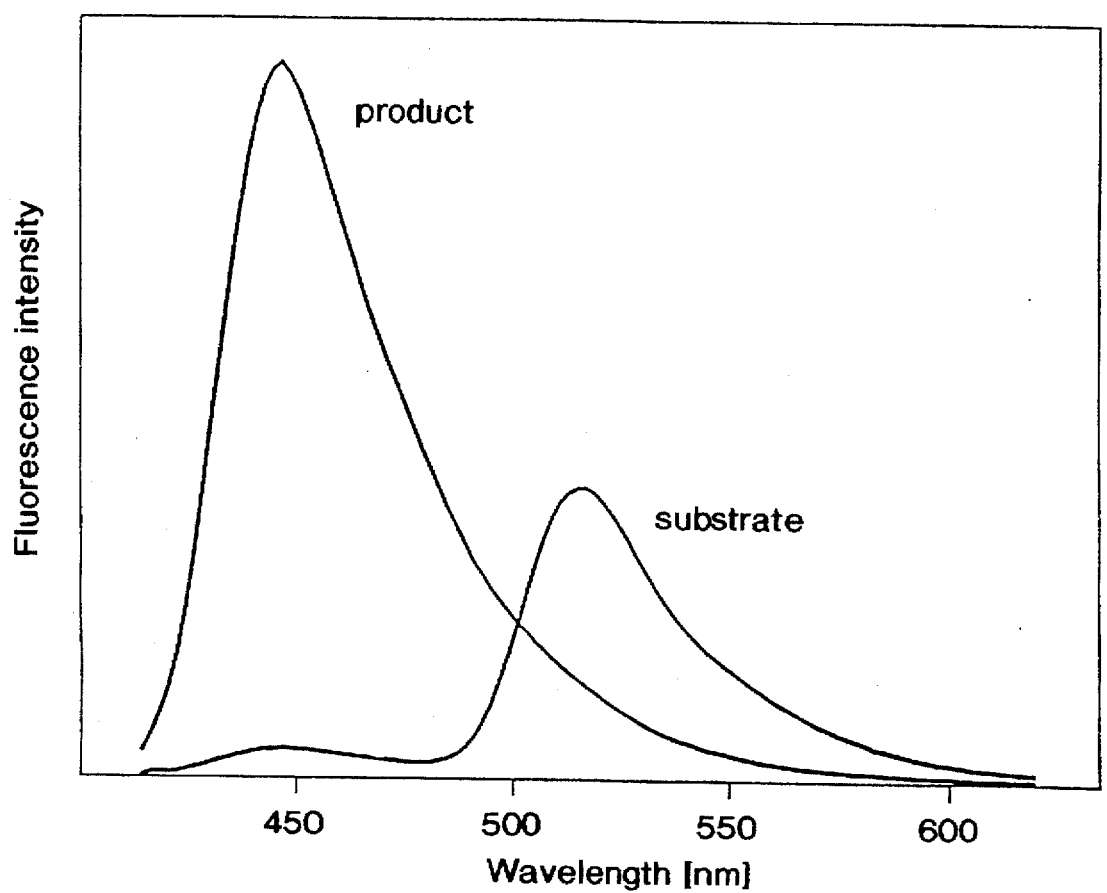
FIG. 5 illustrates the emission spectrum of compound CCF2 before and after β-lactamase cleavage of the β-lactam ring.

FIG. 5 illustrates the emission spectrum of compound CCF2 in 50 mmolar phosphate buffer pH 7.0 before and after β-lactamase cleavage of the β-lactam ring. In the intact substrate, efficient energy transfer occurs from the 7-hydroxycoumarin moiety to the fluorescein moiety. Excitation of the substrate at 405 nm results in fluorescence emission at 515 nm (green) from the acceptor dye fluorescein. The energy transfer is disrupted when β-lacatamase cleaves the β-lactam ring, thereby severing the link between the two dyes. Excitation of the products at 405 nm now results entirely in donor fluorescence emission at 448 nm (blue). The fluorescence emission from the donor moiety increases 25 fold upon β-lactam cleavage. The fluorescence at 515 nm is reduced by 3.5 fold, all of the remaining fluorescence originating from the 7-hydroxycoumarin as its emission spectrum extends into the green. Twenty-five-fold quenching of the donor in the substrate is equivalent to an efficiency of fluorescence energy transfer of 96%. This large fluorescence change upon β-lactam cleavage can readily be used to detect β-lactamase in the cytoplasm of living mammalian cells, as is reported in Examples 6 and 7.

The 7-hydroxycoumarin moiety in the cephalosporin was determined to have a fluorescence quantum efficiency in the absence of the acceptor of 98–100%. This value was determined by comparing the integral of the corrected fluorescence emission spectrum of the dye with that of a solution of 9-aminoacridine hydrochloride in water matched for absorbance at the excitation wavelength. It follows that 7-hydroxycoumarin is an ideal donor dye, as virtually every photon absrobed by the dye undergoes fluorescence energy transfer to the acceptor.

Example 6

Cells of the T-cell lymphoma line Jurkat were suspended in an isotonic saline solution (Hank's balanced salt solution) containing approximately $10^{12}$ β-lactamase enzyme molecules per milliliter (approximately 1.7 nM; Penicillinase 205 TEM $R^+$, from Sigma) and 1 mg/ml rhodamine conjugated to dextran (40 kd) as a marker of loading. The suspension was passed through a syringe needle (30 gauge) four times. This causes transient, survivable disruptions of the cells' plasma membrane and allows entry of labeled dextran and β-lactamase. Cells that had been successfully permeabilized contained β-lactamase and were red fluorescent when illuminated at the rhodamine excitation wavelength on a fluorescent microscope. The cells were incubated with 5 μM fluorogenic β-lactamase substrate, CCF2/$ac_2AM_2$, at room temperature for 30 minutes. Illumination with violet light (405 nm) revealed blue fluorescent and green fluorescent cells. All cells that had taken up the market rhodamine-dextran appeared fluorescent blue, while cells devoid the enzyme appeared fluorescent green.

Example 7

Cells from cell lines of various mammalian origin were transiently transfected with a plasmid containing the β-lactamase gene under the control of a mammalian promotor. 10 to 48 hours after transfection cells were exposed to 5 μmol CCF2/$ac_2AM_2$ for 1 to 6 hours. In all cases fluorescent blue cells were detected on examination with a fluorescence microscope. Not a single blue fluorescent cell was ever detected in nontransfected control cells. To quantitate the fluorescence measurements the cells were first viewed through coumarin (450 DF 65) and then fluorescein (515 EFLP) emission filters and pictures were recorded with a charge couple device camera. The average pixel intensities of CCF2 loaded transfected cells (blue) and controls (green) at coumarin and fluorescein wavelength in COS-7 (Table 2) and CHO (Table 3) cells are summarized; values for 4 representative cells for each population are given. Thus, the substrate CCF2 revealed gene expression in single living mammalian cells.

TABLE 2

COS-7 (origin: SV40 transformed african green monkey kidney cells)

| Table of pixel intensities | | coumarin emission filter | fluorescein emission filter |
|---|---|---|---|
| Blue cell | #1 | 27 | 20 |
| | #2 | 34 | 23 |
| | #3 | 31 | 31 |
| | #4 | 22 | 33 |
| Green cell | #1 | 4 | 43 |
| | #2 | 4 | 42 |
| | #3 | 5 | 20 |
| | #4 | 3 | 24 |

TABLE 3

CHO (origin: Chinese hamster ovary cells)

| Table of pixel intensities | | coumarin emission filter | fluorescein emission filter |
|---|---|---|---|
| Blue cell | #1 | 98 | 112 |
| | #2 | 70 | 113 |
| | #3 | 76 | 92 |
| | #4 | 56 | 67 |
| Green cell | #1 | 9 | 180 |
| | #2 | 9 | 102 |
| | #3 | 7 | 101 |
| | #4 | 9 | 83 |

Example 8

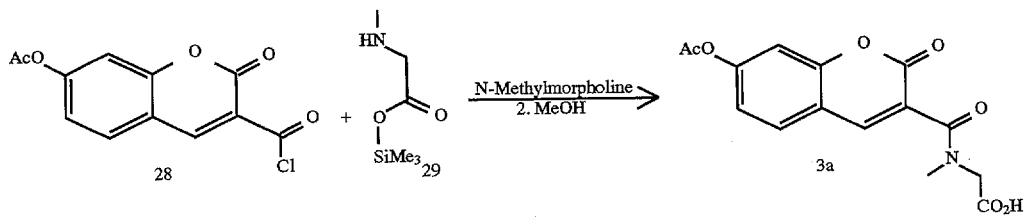

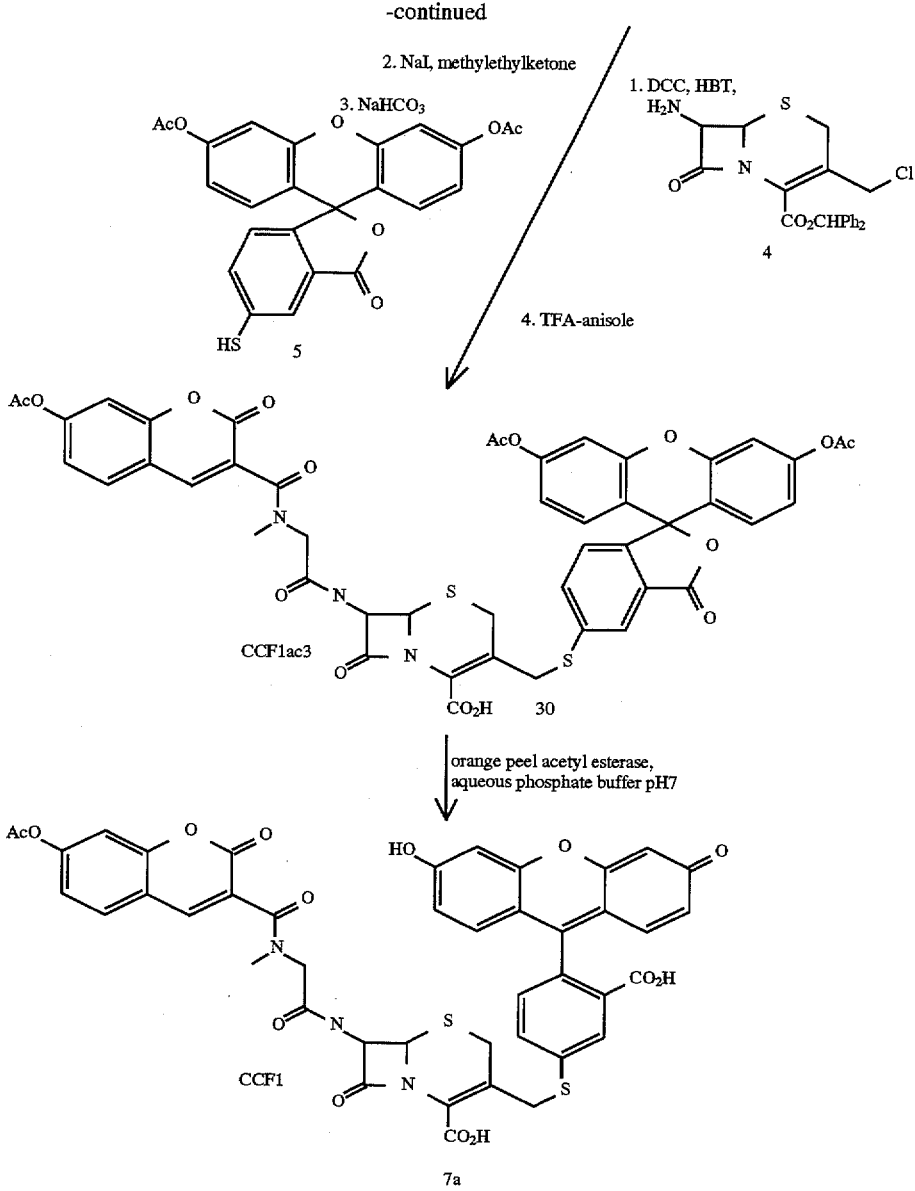

For preparation of 7-Acetyloxy 3-(carbonyl N-methyl glycine) coumarin, 400 mg (1.6 mMol) 3-Carboxy-7-acetylcoumarin were refluxed with 4 ml thionyl chloride for 20 minutes. Excess thionyl chloride was removed by distillation and the residue stored in vacuo over potassium hydroxide pellets overnight. In a separate vessel 142.5 mg (1.6 mMol) sarcosine was dissolved in 1.05 ml (5.4 mMol) N-methyl trimethylsilyl trifluoroacetamide (MSTFA) and kept at room temperature for 16 hours. 2 ml dry acetonitrile and 187 µl (1.7 mMol) N-methylmorpholine were added and the solution was poured onto the solid 3-carbonylchloride-7-acetylcoumarin on ice. After stirring for 20 minutes on ice the solution was let to warm to room temperature. After 4 hours the solvents were removed in vacuo. The residue was dissolved in methanol to deprotect the acid after which the solvent was removed in vacuo. The solid was dissolved in 30 ml ethylacetate-acetonitrile (2:1) and the solution extracted twice with an equal volume of 1N hydrochloric acid and the with brine. The organic phase was dried over anhydrous sodium sulfate. The solvent was removed in vacuo and the solid crystallized from boiling ethylacetate with addition of hexane. The yield was 316 mg (1.0 mMol, 63%) of a white crystalline solid.

Coupling of 7-Acetyloxy 3-(carbonyl N-methyl glycine) coumarin with 7-amino 3'-chloro cephalosporanic acid benzhydryl ester was effected as follows. 62 mg (0.2 mMol) 7-Acetyloxy 3-(carbonyl N-methyl glycine) coumarin was stirred with 1 ml dry methylene chloride to which 27 mg (0.2 mMol) hydroxybenztriazole and 41 mg dicyclohexyl carbodiimide had been added. A solution of 82.6 mg (0.2 mMol) 7-amino 3'-chloro cephalosporanic acid benzhydryl ester in 1 ml methylene chloride was added dropwise over a period of 5 minutes. The reaction was stirred for 20 hours at room temperature after which the precipitate was removed by filtration. The filtrate was evaporated in vacuo and the product extracted into methylene chloride. The solvent was removed once more and the residue dissolved in 1 ml ethyl acetate. Addition of three volumes of hexane precipitated the product which was recovered by centrifugation. The yield was 49.9 mg (70 µMol, 35%) of the product as a white powder.

Conversion of the cephalosporin 3'-chloro substituent in the above product to the 3'-iodo substituent was carried out as follows. 49.9 mg (70 µMol) of the above product was stirred with 52.5 mg sodium iodide (5 equivalents) in 1.2 ml dry methyl ethyl ketone at room temperature for 2 hours. The solvent was removed in vacuo and the residue dissolved in 2 ml ethyl acetate-methylene chloride (1:1) and extracted with cold 2% aqueous sodium thiosulfate solution, followed by two extractions with brine. The organic layer was dried over anhydrous sodium sulfate. The slightly orange powder (32 mg, 40 µMol, 57%) was used without further purification in the next reaction.

Coupling of above product with 5-mercaptofluorescein diacetate (product CCF1ac$_3$ diphenylmethyl ester) was effected by dissolving 32 mg (40 µMol) of the iodo derivative in 0.4 ml dimethylformamide and 3.4 mg sodium bicarbonate added. 22 mg (50 µMol) 5-mercaptofluorescein diacetate were dissolved in 0.3 ml deoxygenated dimethyl formamide and added to the iodo compound in an argon atmosphere. After 2 hours the solvent was removed in vacuo. The residue was suspended in methylene chloride-ethyl acetate (1:1). The organic solution was washed with water and dried over anhydrous sodium sulfate. The solvent was removed and the residue was triturated with ethyl ether hexane (1:1). Flash chromatography on 60 mesh silica gel with ethyl acetate-toluene (2:1) yielded 4.2 mg (4 µMol, 10%) of colorless product.

Cleavage of the diphenylmethyl ester to give CCF1ac$_3$ was effected as follows. 4 mg (4 µMol) of CCF1ac$_3$ diphenylmethyl ester were treated with 200 µl trifluoroacetic acid-anisole-methylene chloride (10:1:10) on ice for 15 minutes. The reagents were removed in vacuo and the residue was dissolved in 0.5 ml ethyl acetate and the solvent evaporated in vacuo. The solid was triturated with ether and then dissolved in 0.5 ml methanol. Addition of the methanolic solution to 2 ml water precipitated the product. The product was recovered by centrifugation and dried in vacuo. The yield was 2 mg (2 µMol, 50%) white solid. The compound was further purified by high performance liquid chromatography on a reverse phase $C_{18}$-column using 55% aqueous acetonitrile containing 05% acetic acid as the eluent.

Figure 6:
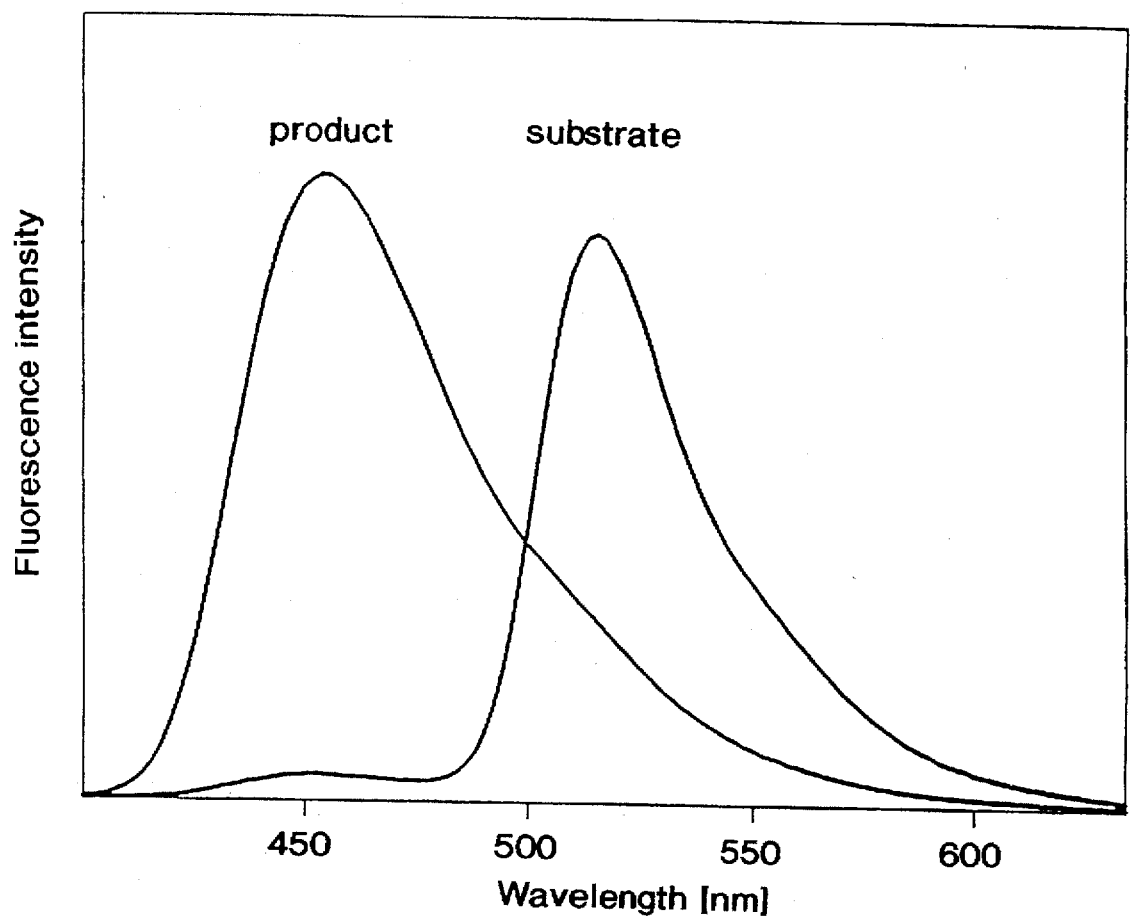
FIG. 6 illustrates the emission spectrum of compound CCF1 before and after β-lactamase cleavage of the β-lactam ring.

The fluorescence emission spectrum of CCF1 before and after β-lactamase cleavage (FIG. 6) was obtained from a sample of CCF1ac$_3$ that had been converted to CCF1 by treatment with orange peel acetyl esterase in 50 mmolar aqueous phosphate buffer pH 7.

Substrate CCF1 has similar fluorescence properties to substrate CCF2 in Example 5. In the intact substrate, efficient energy transfer occurs from the 7-hydroxycoumarin moiety to the fluorescein moiety. Excitation of the substrate at 390 nm results in fluorescence emission at 515 nm (green) from the acceptor dye fluorescein. The energy transfer is disrupted when lactamase cleaves the β-lactam ring, thereby severing the link between the two dyes. Excitation of the products at 390 nm now results entirely in donor fluorescence emission at 460 nm (blue). The fluorescence emission from the donor moiety increases 25-fold upon β-lactam cleavage. The fluorescence at 515 nm is reduced by 3-fold, all of the remaining fluorescence originating from the 7-hydroxycoumarin as its emission spectrum extends into the green. Twenty-five-fold quenching of the donor in the substrate is equivalent to an efficiency of fluorescence energy transfer of 96%. This large fluorescence change upon β-lactam cleavage can readily be used to detect β-lactamase in the cytoplasm of living mammalian cells, as is reported in Example 9.

Example 9

Cells of the T-cell lymphoma line Jurkat were suspended in an isotonic saline solution (Hank's balanced salt solution) containing approximately $10^{12}$ β-lactamase enzyme molecules per milliliter (approximately 1.7 nM; Penicillinase 205 TEM R$^+$, from Sigma) and 1 mg/ml rhodamine conjugated to dextran (40 kd) as a marker of loading. The suspension was passed through a syringe needle (30 gauge) four times. This causes transient, survivable disruptions of the cells' plasma membrane and allows entry of labeled dextran and β-lactamase. Cells which had been successfully permeabilized contained β-lactamase and were red fluorescent when illuminated at the rhodamine excitation wavelength on a fluorescent microscope. The cells were incubated with 30 µM fluorogenic β-lactamase substrate CCF1ac$_3$ at room temperature for 30 minutes. Illumination with ultraviolet light (360 nm) revealed blue fluorescent and green fluorescent cells. All cells that had taken up the marker rhodamine-dextran appeared fluorescent blue, while cells devoid the enzyme appeared fluorescent green.

From the foregoing description, one skilled in the art can readily ascertain the essential characteristics of the invention and, without departing from the spirit and scope thereof can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A compound having the formula I:

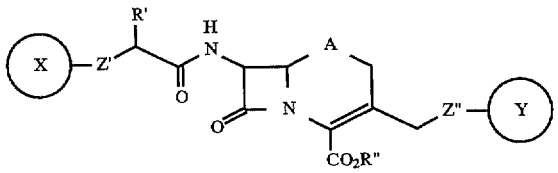

wherein:
one of X and Y is a fluorescent donor moiety or an ester derivative of said fluorescent donor moiety, and the other is a quencher or an ester derivative of said quencher; wherein said quencher quenches fluorescence of said fluorescent donor moiety;

R' is selected from the group consisting of H, lower alkyl and $(CH_2)_nOH$, in which n is 0 or an integer from 1 to 5;

R" is selected from the group consisting of H, physiologically acceptable metal and ammonium cations, $-CHR^2OCO(CH_2)_nCH_3$, $-CHR^2OCOC(CH_3)_3$, -acylthiomethyl, -acyloxy-alpha-benzyl, -delta-butyrolactonyl, -methoxycarbonyloxymethyl, -phenyl, -methylsulphinylmethyl, -beta-morpholinoethyl, -dialkylaminoethyl, -acyloxyalkyl, -dialkylaminocarbonyloxymethyl and -alkyl, in which $R^2$ is selected from the group consisting of H and lower alkyl and in which n is 0 or an integer from 1 to 5; A is selected from the group consisting of S, O, SO, $SO_2$ and $CH_2$; and Z' and Z" are linkers for the fluorescent donor and quencher moieties.

2. The compound of claim 1, wherein Z' is selected from the group consisting of a direct bond $-(CH_2)_nCONR^2(CH_2)$ $_m$—, —(CH$_2$)$_n$NR$^2$CO(CH$_2$)$_m$—, —(CH$_2$)$_n$NR$^2$CONR$^2$(CH$_2$)$_m$—, —(CH$_2$)$_n$NR$^3$CSNR$^2$(CH$_2$)$_m$—, —(CH$_2$)$_n$CONR$^3$(CH$_2$)$_p$CONR$^2$(CH$_2$)$_m$—, —(CH$_2$)$_n$—, —(CH$_2$)$_n$NR$^3$CO(CH$_2$)$_p$S(CH$_2$)$_m$—, —(CH$_2$)$_n$S(CH$_2$)$_m$—, —(CH$_2$)$_n$O(CH$_2$)$_m$—, —(CH$_2$)$_n$NR$^2$(CH$_2$)$_m$—, —(CH$_2$)$_n$SO$_2$NR$^2$(CH$_2$)$_m$—, —(CH$_2$)$_n$CO$_2$(CH$_2$)$_m$—, and

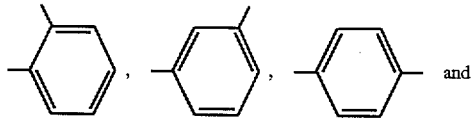, and

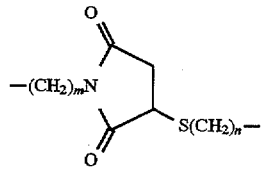

in which R$^2$ is selected from the group consisting of H and lower alkyl; R$^3$ is selected from the group consisting of hydrogen and lower alkyl; and each of n, m and p is independently selected from the group consisting of 0 and integers from 1 to 4.

3. The compound of claim 1, wherein Z" is selected from the group consisting of a direct bond to a heteroatom in Y, —O(CH$_2$)$_n$—, —S(CH$_2$)$_n$—, —NR$^2$(CH$_2$)$_n$—, —N$^+$R$^2$$_2$(CH$_2$)$_n$—, —OCONR$^2$(CH$_2$)$_n$—, —O$_2$C(CH$_2$)$_n$—, —SCSNR$^2$(CH$_2$)$_n$—, —SCSO(CH$_2$)$_n$—, and

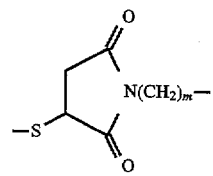

in which R$^2$ is selected from the group consisting of H and lower alkyl; and each of n and m is independently selected from the group consisting of 0 and integers from 1 to 4.

4. The compound of claim 1, wherein said quencher is an acceptor for said fluorescent donor moiety in a FRET pair.

5. The compound of claim 4, wherein at least one of said X and Y is membrane-permeant.

6. The compound of claim 4, wherein at least one of said X and Y is an ester derivative of said fluorescent donor or said acceptor.

7. The compound of claim 6, wherein said fluorescent donor or acceptor is selected from the group consisting of coumarin dye, acridine dye, rhodamine dye fluorescein dye, eosin dye and rhodol dye.

8. The compound of claim 6, wherein said compound is located within a living cell.

9. The compound of claim 1, wherein said compound is selected from the group consisting of:

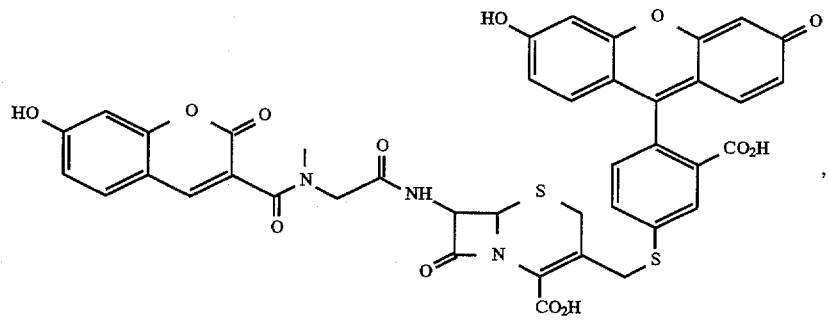,

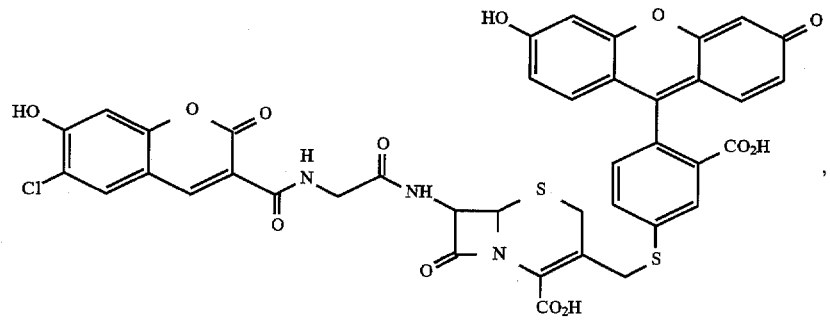,

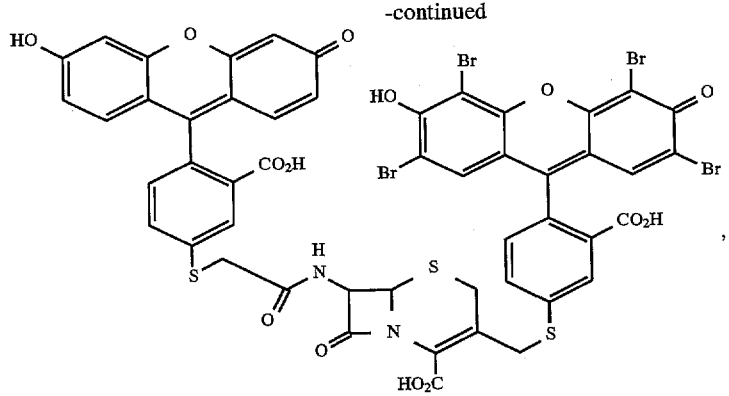
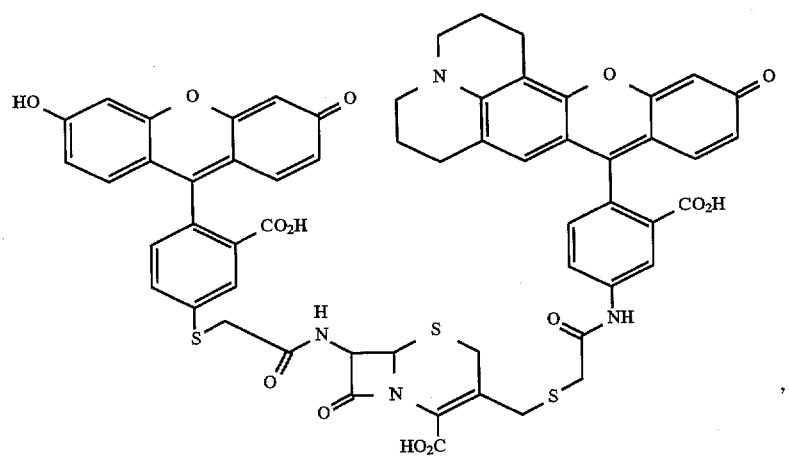
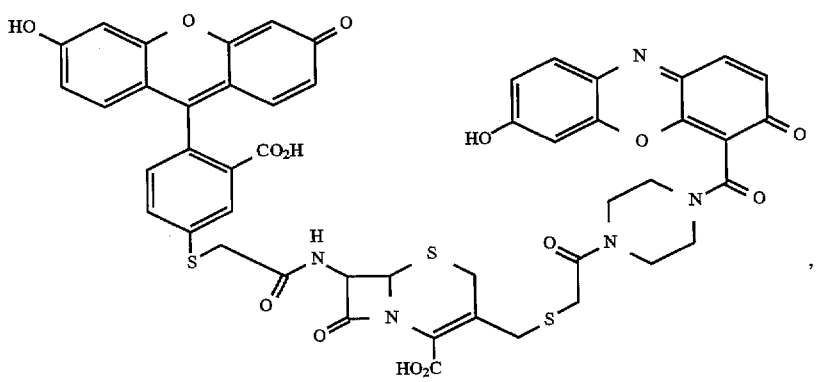
and ester derivatives thereof.
10. The compound of claim 9, wherein said compound is membrane-permeant.
11. The compound of claim 9, wherein said compound is

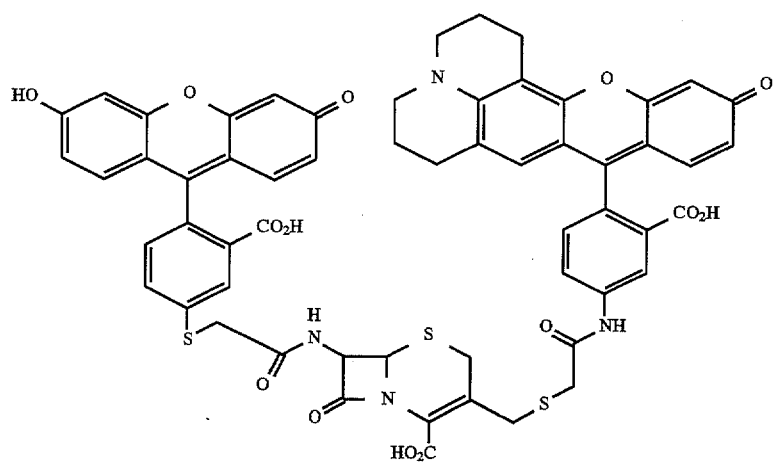
12. The compound of claim 9, wherein said compound is
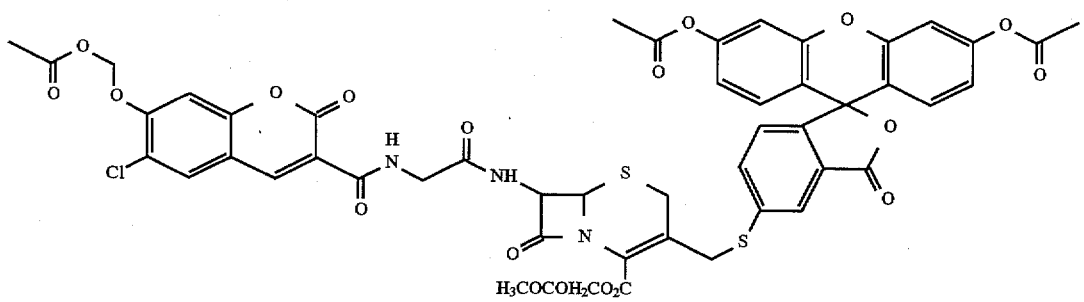
13. The compound of claim 9, wherein said compound is
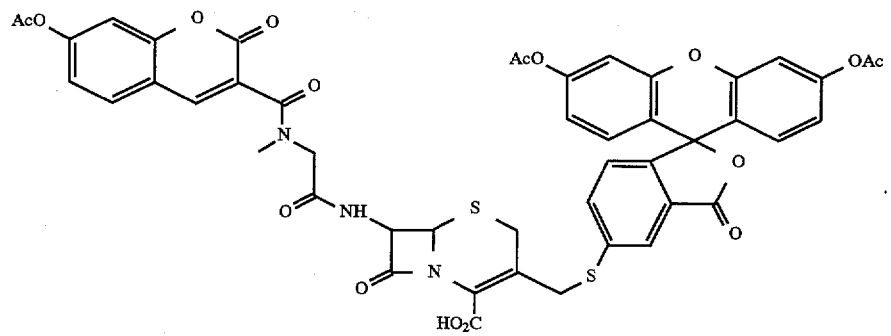
14. A compound selected from the group consisting of:

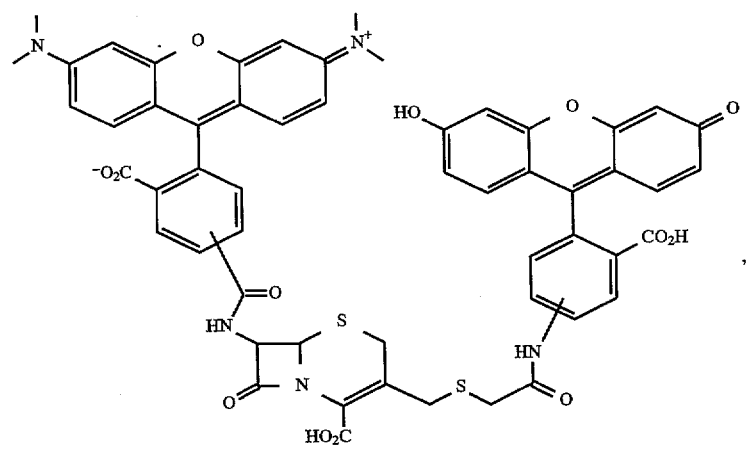
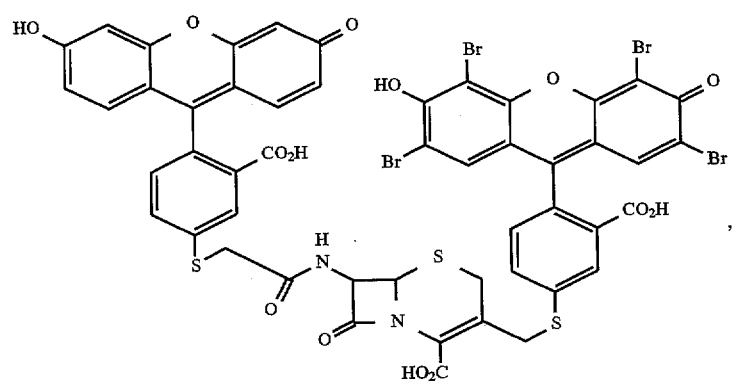
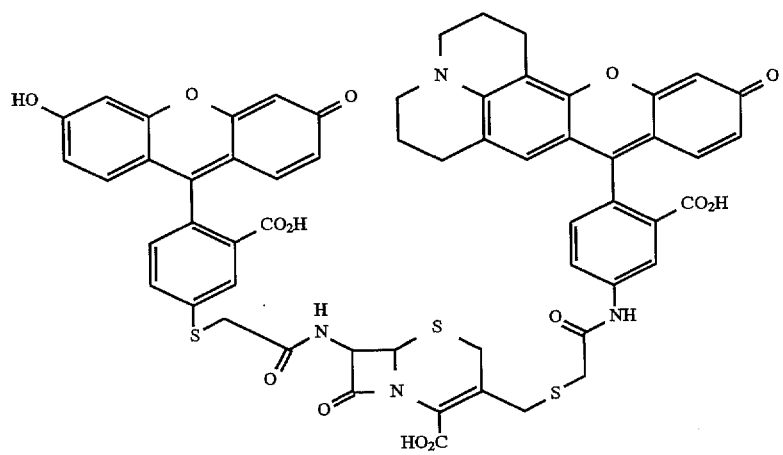

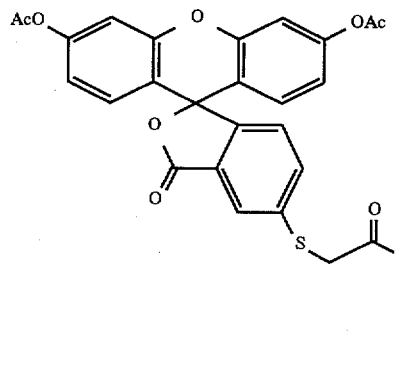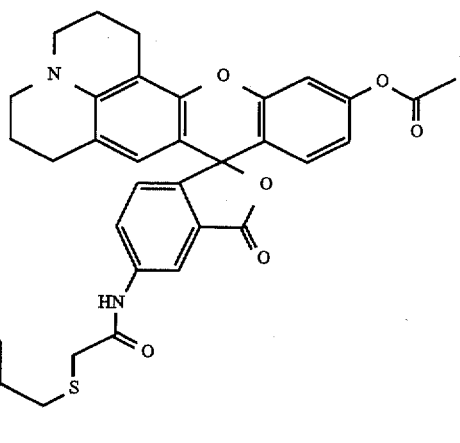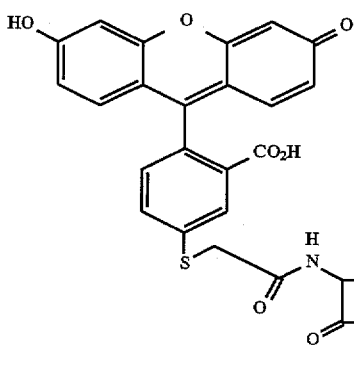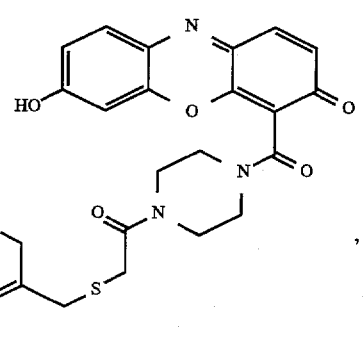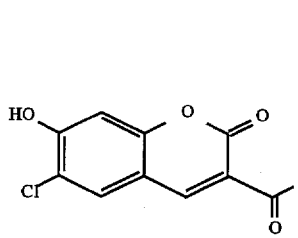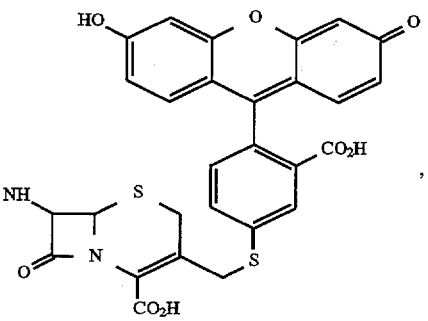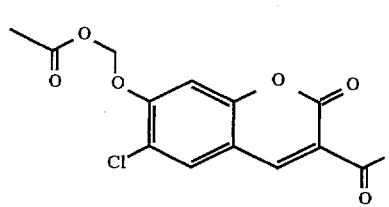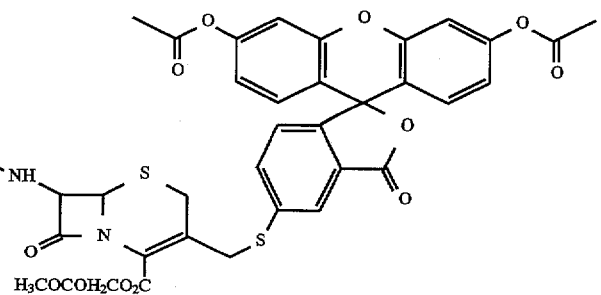

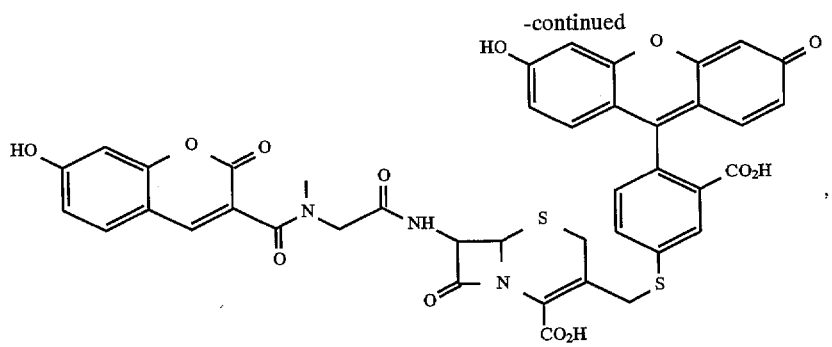

and

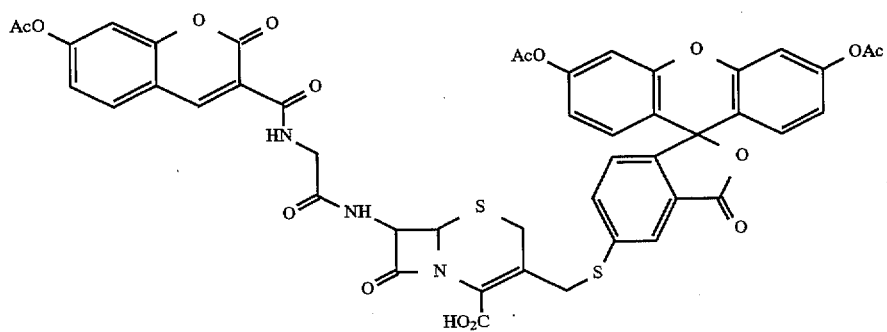

15. A method for detecting the presence of beta-lactamase activity in a sample, comprising:

contacting the sample with at least one compound of general formula I

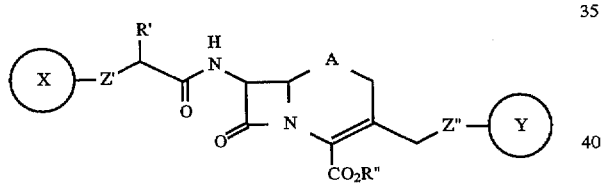

wherein:

one of X and Y is a fluorescent donor moiety or an ester said fluorescent donor moiety, and the other is a quencher or an ester derivative of said quencher; wherein said quencher quenches fluorescence of said fluorescent donor moiety;

R' is selected from the group consisting of H, lower alkyl and $(CH_2)_nOH$, in which n is 0 or an integer from 1 to 5;

R" selected from the group consisting of H, physiologically acceptable metal and ammonium cations, —$CHR_2OCO(CH_2)_nCH_3$, —$CHR^2OCOC(CH_3)_3$, -acylthiomthyl, -aeyloxy-alpha-benzyl, -delta-butyrolactonyl, -methoxycarbonyloxymethyl, -phenyl, methylsulphinylmethyl, -beta-morpholinoethyl, -dialkylaminoethyl, -acyloxyalkyl, -dialkylaminocarbonyloxymethyl and -alkyl, in which $R^2$ is selected from the group consisting of H and lower alkyl and in which n is 0 or an integer from 1 to 5; A is selected from the group consisting of S, O, SO, $SO_2$ and $CH_2$ and Z' and Z" are linkers for the fluorescent donor and quencher moieties; and determining a fluorescence property or fluorescence spectrum of the sample.

16. The method of claim 15, wherein said sample has a β-lactamase reporter gene.

17. The method of claim 10, wherein said β-lactamase reporter gene is in a mammalian cell.

18. The method of claim 17, wherein said determining step measures FRET.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 798 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
(A) NAME/KEY: CDS
(B) LOCATION: 7..795

( x i ) SEQUENCE DESCRIPTION: SEQ ID NO:1:

| ATGAGT | CAC<br>His<br>1 | CCA<br>Pro | GAA<br>Glu | ACG<br>Thr | CTG<br>Leu<br>5 | GTG<br>Val | AAA<br>Lys | GTA<br>Val | AAA<br>Lys | GAT<br>Asp<br>10 | GCT<br>Ala | GAA<br>Glu | GAT<br>Asp | CAG<br>Gln | 48 |
|---|---|---|---|---|---|---|---|---|---|---|---|---|---|---|---|
| TTG<br>Leu<br>15 | GGT<br>Gly | GCA<br>Ala | CGA<br>Arg | GTG<br>Val<br>20 | GGT<br>Gly | TAC<br>Tyr | ATC<br>Ile | GAA<br>Glu | CTG<br>Leu<br>25 | GAT<br>Asp | CTC<br>Leu | AAC<br>Asn | AGC<br>Ser | GGT<br>Gly | AAG<br>Lys<br>30 | 96 |
| ATC<br>Ile | CTT<br>Leu | GAG<br>Glu | AGT<br>Ser | TTT<br>Phe<br>35 | CGC<br>Arg | CCC<br>Pro | GAA<br>Glu | GAA<br>Glu | CGT<br>Arg<br>40 | TTT<br>Phe | CCA<br>Pro | ATG<br>Met | ATG<br>Met | AGC<br>Ser | ACT<br>Thr<br>45 | 144 |
| TTT<br>Phe | AAA<br>Lys | GTT<br>Val | CTG<br>Leu<br>50 | CTA<br>Leu | TGT<br>Cys | GGC<br>Gly | GCG<br>Ala | GTA<br>Val<br>55 | TTA<br>Leu | TCC<br>Ser | CGT<br>Arg | GTT<br>Val | GAC<br>Asp<br>60 | GCC<br>Ala | GGG<br>Gly | 192 |
| CAA<br>Gln | GAG<br>Glu | CAA<br>Gln<br>65 | CTC<br>Leu | GGT<br>Gly | CGC<br>Arg | CGC<br>Arg | ATA<br>Ile<br>70 | CAC<br>His | TAT<br>Tyr | TCT<br>Ser | CAG<br>Gln | AAT<br>Asn<br>75 | GAC<br>Asp | TTG<br>Leu | GTT<br>Val | 240 |
| GAG<br>Glu | TAC<br>Tyr<br>80 | TCA<br>Ser | CCA<br>Pro | GTC<br>Val | ACA<br>Thr | GAA<br>Glu<br>85 | AAG<br>Lys | CAT<br>His | CTT<br>Leu | ACG<br>Thr | GAT<br>Asp<br>90 | GGC<br>Gly | ATG<br>Met | ACA<br>Thr | GTA<br>Val | 288 |
| AGA<br>Arg<br>95 | GAA<br>Glu | TTA<br>Leu | TGC<br>Cys | AGT<br>Ser | GCT<br>Ala<br>100 | GCC<br>Ala | ATA<br>Ile | ACC<br>Thr | ATG<br>Met | AGT<br>Ser<br>105 | GAT<br>Asp | AAC<br>Asn | ACT<br>Thr | GCG<br>Ala | GCC<br>Ala<br>110 | 336 |
| AAC<br>Asn | TTA<br>Leu | CTT<br>Leu | CTG<br>Leu | ACA<br>Thr<br>115 | ACG<br>Thr | ATC<br>Ile | GGA<br>Gly | GGA<br>Gly | CCG<br>Pro<br>120 | AAG<br>Lys | GAG<br>Glu | CTA<br>Leu | ACC<br>Thr | GCT<br>Ala | TTT<br>Phe<br>125 | 384 |
| TTG<br>Leu | CAC<br>His | AAC<br>Asn | ATG<br>Met<br>130 | GGG<br>Gly | GAT<br>Asp | CAT<br>His | GTA<br>Val | ACT<br>Thr<br>135 | CGC<br>Arg | CTT<br>Leu | GAT<br>Asp | CGT<br>Arg | TGG<br>Trp<br>140 | GAA<br>Glu | CCG<br>Pro | 432 |
| GAG<br>Glu | CTG<br>Leu | AAT<br>Asn<br>145 | GAA<br>Glu | GCC<br>Ala | ATA<br>Ile | CCA<br>Pro<br>150 | AAC<br>Asn | GAC<br>Asp | GAG<br>Glu | CGT<br>Arg | GAC<br>Asp<br>155 | ACC<br>Thr | ACG<br>Thr | ATG<br>Met | CCT<br>Pro | 480 |
| GCA<br>Ala<br>160 | GCA<br>Ala | ATG<br>Met | GCA<br>Ala | ACA<br>Thr | ACG<br>Thr<br>165 | TTG<br>Leu | CGC<br>Arg | AAA<br>Lys | CTA<br>Leu | TTA<br>Leu<br>170 | ACT<br>Thr | GGC<br>Gly | GAA<br>Glu | CTA<br>Leu | CTT<br>Leu | 528 |
| ACT<br>Thr<br>175 | CTA<br>Leu | GCT<br>Ala | TCC<br>Ser | CGG<br>Arg | CAA<br>Gln<br>180 | CAA<br>Gln | TTA<br>Leu | ATA<br>Ile | GAC<br>Asp | TGG<br>Trp<br>185 | ATG<br>Met | GAG<br>Glu | GCG<br>Ala | GAT<br>Asp | AAA<br>Lys<br>190 | 576 |
| GTT<br>Val | GCA<br>Ala | GGA<br>Gly | CCA<br>Pro | CTT<br>Leu<br>195 | CTG<br>Leu | CGC<br>Arg | TCG<br>Ser | GCC<br>Ala | CTT<br>Leu<br>200 | CCG<br>Pro | GCT<br>Ala | GGC<br>Gly | TGG<br>Trp | TTT<br>Phe | ATT<br>Ile<br>205 | 624 |
| GCT<br>Ala | GAT<br>Asp | AAA<br>Lys | TCT<br>Ser<br>210 | GGA<br>Gly | GCC<br>Ala | GGT<br>Gly | GAG<br>Glu | CGT<br>Arg<br>215 | GGG<br>Gly | TCT<br>Ser | CGC<br>Arg | GGT<br>Gly | ATC<br>Ile<br>220 | ATT<br>Ile | GCA<br>Ala | 672 |
| GCA<br>Ala | CTG<br>Leu | GGG<br>Gly<br>225 | CCA<br>Pro | GAT<br>Asp | GGT<br>Gly | AAG<br>Lys | CCC<br>Pro<br>230 | TCC<br>Ser | CGT<br>Arg | ATC<br>Ile | GTA<br>Val | GTT<br>Val<br>235 | ATC<br>Ile | TAC<br>Tyr | ACG<br>Thr | 720 |
| ACG<br>Thr | GGG<br>Gly<br>240 | AGT<br>Ser | CAG<br>Gln | GCA<br>Ala | ACT<br>Thr<br>245 | ATG<br>Met | GAT<br>Asp | GAA<br>Glu | CGA<br>Arg | AAT<br>Asn<br>250 | AGA<br>Arg | CAG<br>Gln | ATC<br>Ile | GCT<br>Ala | GAG<br>Glu | 768 |
| ATA<br>Ile<br>255 | GGT<br>Gly | GCC<br>Ala | TCA<br>Ser | CTG<br>Leu | ATT<br>Ile<br>260 | AAG<br>Lys | CAT<br>His | TGG<br>Trp | TAA | | | | | | | 798 |

( 2 ) INFORMATION FOR SEQ ID NO:2:

( i ) SEQUENCE CHARACTERISTICS:
(A) LENGTH: 263 amino acids (B) TYPE: amino acid
(D) TOPOLOGY: linear (ii) MOLECULE TYPE: protein (xi) SEQUENCE DESCRIPTION: SEQ ID NO:2:

```
His Pro Glu Thr Leu Val Lys Val Lys Asp Ala Glu Asp Gln Leu Gly
 1               5                   10                  15
Ala Arg Val Gly Tyr Ile Glu Leu Asp Leu Asn Ser Gly Lys Ile Leu
            20                  25                  30
Glu Ser Phe Arg Pro Glu Glu Arg Phe Pro Met Met Ser Thr Phe Lys
        35                  40                  45
Val Leu Leu Cys Gly Ala Val Leu Ser Arg Val Asp Ala Gly Gln Glu
    50                  55                  60
Gln Leu Gly Arg Arg Ile His Tyr Ser Gln Asn Asp Leu Val Glu Tyr
65                  70                  75                  80
Ser Pro Val Thr Glu Lys His Leu Thr Asp Gly Met Thr Val Arg Glu
                85                  90                  95
Leu Cys Ser Ala Ala Ile Thr Met Ser Asp Asn Thr Ala Ala Asn Leu
            100                 105                 110
Leu Leu Thr Thr Ile Gly Gly Pro Lys Glu Leu Thr Ala Phe Leu His
        115                 120                 125
Asn Met Gly Asp His Val Thr Arg Leu Asp Arg Trp Glu Pro Glu Leu
    130                 135                 140
Asn Glu Ala Ile Pro Asn Asp Glu Arg Asp Thr Thr Met Pro Ala Ala
145                 150                 155                 160
Met Ala Thr Thr Leu Arg Lys Leu Leu Thr Gly Glu Leu Leu Thr Leu
                165                 170                 175
Ala Ser Arg Gln Gln Leu Ile Asp Trp Met Glu Ala Asp Lys Val Ala
            180                 185                 190
Gly Pro Leu Leu Arg Ser Ala Leu Pro Ala Gly Trp Phe Ile Ala Asp
        195                 200                 205
Lys Ser Gly Ala Gly Glu Arg Gly Ser Arg Gly Ile Ile Ala Ala Leu
    210                 215                 220
Gly Pro Asp Gly Lys Pro Ser Arg Ile Val Val Ile Tyr Thr Thr Gly
225                 230                 235                 240
Ser Gln Ala Thr Met Asp Glu Arg Asn Arg Gln Ile Ala Glu Ile Gly
                245                 250                 255
Ala Ser Leu Ile Lys His Trp
            260
```